United States Patent
Jain et al.

(10) Patent No.: US 11,666,546 B2
(45) Date of Patent: Jun. 6, 2023

(54) GHB PHARMACEUTICAL COMPOSITIONS COMPRISING A FLOATING INTERPENETRATING POLYMER NETWORK FORMING SYSTEM

(71) Applicant: Tris Pharma, Inc., Monmouth Junction, NJ (US)

(72) Inventors: Paras Rameshlal Jain, Dayton, NJ (US); Sachin Vasant Chaudhari, Monmouth Junction, NJ (US)

(73) Assignee: TRIS PHARMA, INC, Monmouth Junction, NJ (US)

(*) Notice: Subject to any disclaimer, the term of this patent is extended or adjusted under 35 U.S.C. 154(b) by 215 days.

(21) Appl. No.: 16/955,389

(22) PCT Filed: Dec. 18, 2018

(86) PCT No.: PCT/US2018/066300
§ 371 (c)(1),
(2) Date: Jun. 18, 2020

(87) PCT Pub. No.: WO2019/126215
PCT Pub. Date: Jun. 27, 2019

(65) Prior Publication Data
US 2021/0069136 A1 Mar. 11, 2021

Related U.S. Application Data

(60) Provisional application No. 62/728,764, filed on Sep. 8, 2018, provisional application No. 62/607,151, filed on Dec. 18, 2017.

(51) Int. Cl.
*A61K 31/19* (2006.01)
*A61K 9/08* (2006.01)
*A61K 9/00* (2006.01)
*A61K 47/36* (2006.01)

(52) U.S. Cl.
CPC ............ *A61K 31/19* (2013.01); *A61K 9/0053* (2013.01); *A61K 9/08* (2013.01); *A61K 47/36* (2013.01)

(58) Field of Classification Search
CPC ................................. A61K 31/19; A61K 9/08
See application file for complete search history.

(56) References Cited

U.S. PATENT DOCUMENTS

| | | |
|---|---|---|
| 3,138,525 A | 6/1964 | Koff |
| 3,499,960 A | 3/1970 | Macek et al. |
| 3,901,232 A | 8/1975 | Michaels et al. |
| 4,221,778 A | 9/1980 | Raghunathan |
| 4,352,891 A | 10/1982 | Quinlan |
| 4,393,236 A | 7/1983 | Klosa |
| 4,575,539 A | 3/1986 | DeCrosta et al. |
| 4,847,077 A | 7/1989 | Raghunathan |
| 4,996,047 A | 2/1991 | Kelleher et al. |
| 5,368,852 A | 11/1994 | Umemoto et al. |
| 5,604,927 A | 2/1997 | Moore |
| 5,780,057 A | 6/1998 | Conte et al. |
| 5,808,107 A | 9/1998 | Hollingsworth |
| 5,908,631 A | 6/1999 | Arnaud et al. |
| 5,972,389 A | 10/1999 | Shell et al. |
| 5,980,882 A | 11/1999 | Eichman |
| 5,990,162 A | 11/1999 | Scharf |
| 6,022,562 A | 2/2000 | Autant et al. |
| 6,120,803 A | 9/2000 | Wong et al. |
| 6,187,323 B1 | 2/2001 | Aiache et al. |
| 6,340,475 B2 | 1/2002 | Shell et al. |
| 6,488,962 B1 | 12/2002 | Barner et al. |
| 6,713,639 B1 | 3/2004 | Gurjar et al. |
| 7,294,347 B2 | 11/2007 | Menjoge et al. |
| 7,405,238 B2 | 7/2008 | Markey et al. |
| 7,413,751 B2 | 8/2008 | Devane et al. |
| 7,682,629 B1 | 3/2010 | Besse |
| 7,906,145 B2 | 3/2011 | Castan et al. |
| 7,910,133 B2 | 3/2011 | Castan et al. |
| 7,976,870 B2 | 7/2011 | Berner et al. |
| 8,062,667 B2 | 11/2011 | Mehta et al. |
| 8,193,211 B2 | 6/2012 | Liang et al. |
| 8,202,542 B1 | 6/2012 | Mehta et al. |
| 8,263,650 B2 | 9/2012 | Cook et al. |
| 8,277,843 B2 | 10/2012 | Singh et al. |
| 8,287,848 B2 | 10/2012 | Mehta et al. |
| 8,313,770 B2 | 11/2012 | Pathak et al. |

(Continued)

FOREIGN PATENT DOCUMENTS

| JP | S62195323 | 8/1987 |
|---|---|---|
| JP | 2008-174511 | 7/2008 |

(Continued)

OTHER PUBLICATIONS

Guar, P. et al. Ion Exchange Resins in Gastroretentive Drug Delivery: Characteristics, Selection, Formulation and Applications *International Journal of Pharmacology and Pharmaceutical Sciences*, Dec. 2014, 1: 304-312.

Patil, J. S. et al. Ionotropic Gelation and Polyelectrolyte Complexation: The Novel Techniques To Design Hydrogel Particulate Sustained, Modulated Drug Delivery System: A Review *Digest Journal of Nanomaterials and Biostructures*, Mar. 2010, 5(1): 241-248.

Thakral, S. et al. Eudragit®: a technology evaluation *Expert Opinion on Drug Delivery*, Oct. 26, 2012, 10(1): 131-149.

Sing, I. et al. Ion Exchange Resins: Drug Delivery and Therapeutic Applications *FABAD J. Pharm. Sci.*, Jul. 2006, 32: 91-100.

(Continued)

*Primary Examiner* — Shawquia Jackson
(74) *Attorney, Agent, or Firm* — Howson & Howson LLP; Cathy A. Kodroff

(57) ABSTRACT

GHB drug delivery systems comprising a floating interpenetrating network (IPN) are provided. The pharmaceutical compositions contain at least one IPN forming system, at least GHB drug, and at least one gas generating agent, such that upon oral ingestion of the compositions, a floating IPN is formed in situ. These floating IPN provide extended release of the GHB drug entrapped therein for at least about 3 hours.

19 Claims, 4 Drawing Sheets

(56) References Cited

U.S. PATENT DOCUMENTS

| | | |
|---|---|---|
| 8,318,210 B2 | 11/2012 | Tengler et al. |
| 8,324,275 B2 | 12/2012 | Cook et al. |
| 8,470,375 B1 | 6/2013 | McMahen et al. |
| 8,512,759 B1 | 8/2013 | McMahen et al. |
| 8,586,083 B2 | 11/2013 | Mohammad |
| 8,591,922 B1 | 11/2013 | Allphin et al. |
| 8,592,481 B2 | 11/2013 | Berner et al. |
| 8,668,929 B2 | 3/2014 | Han et al. |
| 8,747,902 B2 | 6/2014 | Mehta et al. |
| 8,778,396 B2 | 7/2014 | Pillay et al. |
| 8,790,700 B2 | 7/2014 | Mehta et al. |
| 8,802,157 B2 | 8/2014 | Berner et al. |
| 8,859,619 B2 | 10/2014 | Cook et al. |
| 8,901,173 B2 | 12/2014 | Allphin et al. |
| 9,000,046 B2 | 4/2015 | Berner et al. |
| 9,132,107 B2 | 9/2015 | Allphin et al. |
| 9,161,911 B2 | 10/2015 | Hou |
| 9,301,934 B2 | 4/2016 | Berner et al. |
| 9,439,851 B2 | 9/2016 | Dharmadhkari et al. |
| 9,566,258 B2 | 2/2017 | Hou |
| 9,555,017 B2 | 12/2017 | Allphin et al. |
| 10,092,511 B2 | 10/2018 | Castan et al. |
| 10,398,662 B1 | 9/2019 | Allphin et al. |
| 11,337,919 B2 | 5/2022 | Jain et al. |
| 11,337,920 B2 | 5/2022 | Jain et al. |
| 2003/0099711 A1 | 5/2003 | Meadows et al. |
| 2004/0092455 A1 | 5/2004 | Mamelak et al. |
| 2004/0219186 A1 | 11/2004 | Ayres |
| 2005/0136114 A1 | 6/2005 | Kulkarni et al. |
| 2006/0062844 A1 | 3/2006 | Chenevier et al. |
| 2006/0210630 A1 | 9/2006 | Liang et al. |
| 2007/0036843 A1 | 2/2007 | Hirsh et al. |
| 2007/0148239 A1 | 6/2007 | Hall et al. |
| 2007/0215511 A1 | 9/2007 | Mehta et al. |
| 2009/0275530 A1 | 11/2009 | Tester et al. |
| 2012/0076865 A1 | 3/2012 | Allphin et al. |
| 2013/0142846 A1 | 6/2013 | Lee et al. |
| 2016/0128981 A1 | 5/2016 | Chen et al. |
| 2016/0228379 A1 | 8/2016 | Kumar et al. |
| 2016/0317388 A1 | 11/2016 | Bhargava et al. |

FOREIGN PATENT DOCUMENTS

| | | |
|---|---|---|
| WO | WO 2007/001300 A1 | 1/2007 |
| WO | WO 2007/010400 | 1/2007 |
| WO | WO 2007/109104 A3 | 9/2007 |
| WO | WO 2011/018582 | 2/2011 |
| WO | WO 2011/119839 A1 | 9/2011 |
| WO | WO 2012/107652 A1 | 8/2012 |
| WO | WO 2013/188413 A1 | 12/2013 |
| WO | WO2015/166473 A1 | 11/2015 |
| WO | WO 2015/186108 A1 | 12/2015 |
| WO | WO 2016/066256 A1 | 5/2016 |
| WO | WO 2016/087952 A1 | 6/2016 |
| WO | WO 2019/126214 A1 | 6/2019 |
| WO | WO 2019/126216 A1 | 6/2019 |
| WO | WO 2019/126218 A1 | 6/2019 |

OTHER PUBLICATIONS

Non-Final Office Action, dated Nov. 10, 2021, issued in U.S. Appl. No. 16/955,373.

Requirement for Unity of Invention, dated Jun. 29, 2021, issued in U.S. Appl. No. 16/955,373.

Non-Final Office Action, dated Jun. 30, 2021, issued in U.S. Appl. No. 16/955,392.

Non-Final Office Action, dated Jul. 7, 2021, issued in U.S. Appl. No. 16/955,377.

Office Action issued in European Patent Application No. 18834152.3, dated May 14, 2021.

Office Action issued in European Patent Application No. 18834153.1, dated May 14, 2021.

Office Action issued in European Patent Application No. 18840118.6, dated May 31, 2021.

Banerjee S et al., Investigation on crosslinking density for development of novel interpenetrating polymer network (IPN) based formulation, Journal of Scientific and Industrial Research, 2010, 69(10):777-784.

Bhardwaj V et al., Interpenetrating Polymer Network (IPN): Novel approach in Drug delivery, Int. J. Drug Dev. Res., 4(3), Jul.-Sep. 2012.

Bhardwaj L et al., A Short Review on Gastro Retentive Formulations for Stomach Specific Drug Delivery: Special Emphasis on Floating In situ Gel Systems, African J of Basic & Applied Sciences, 2011, 3(6):300-312.

Hanninen K et al., Mechanistic evaluation of factors affecting compound loading into ion-exchange fibers, Eur. J. Pharm. Sci., 2007, 31(5): 306-317.

Koul V et al., Interpenetrating polymer network (IPN) nanogels based on gelatin and poly(acrylic acid) by inverse mini-emulsion technique: synthesis and characterization, Colloids Surf. B. Biointerfaces, 2011, 83(2):2014-213.

Koshmala JD et al., Preparation of interpenetrating networks of gelatin and dextran as degradable biomaterials, Biomaterials, 2000, 21(20) :2019-2023.

Landfester K et al., Synthesis of colloidal particles in miniemulsions, Annual Review of Materials Research, 2006, 36:231-279.

Lohani A et al., Interpenetrating Polymer Networks as Innovative Drug Delivery Systems, Journal of Drug Delivery, 2014, 2014:1-11.

Lu J et al., One-step synthesis of interpenetrating network hydrogels: Environment sensitivities and drug delivery properties, Saudi J. Biol. Sci. 2016, 2016(3):S22-S31.

Nirmal HB et al., In-Situ gel: New trends in Controlled and Sustained Drug Delivery System, Int. J. of PharmTech Research, 2010, 2(2):1398-1408.

Yashwantrao PA et al., A Raft Forming System: An Novel Approach for Gastroretention, Int. J. Pure App. Biosci., 2015, 3(4):178-192.

Shailaja P et al., A Review on Gastroretentive Drug Delivery System, International Journal of Research and Development in Pharmacy and Life Sciences, 2016, 5(4):2178-2187.

Sharma AR and Khan A, Gastroretentive Drug Delivery System: An Approach to Enhance Gastric Retention for Prolonged Drug Release, International Journal of Pharmaceutical Sciences and Research, 2014, 5(4):1095-1106.

Subrahmanyam PJ, Design and development of guar gum and borax crosslinked guar gum matrix tablets of theophylline for colon specific drug, Journal of Chemical and Pharmaceutical Research, 2012, 4(2):1052-1060.

Rajesh AM et al, Taste masking of ciprofloxacin by ion-exchange resin and sustain release at gastric-intestinal through interpenetrating polymer network, Asian Journal of Pharmaceutical Sciences, 2015, 10(2015):331-340.

Rajesh AM et al, Taste masking of ofloxacin and formation of interpenetrating polymer network beads for sustained release, Journal of Pharmaceutical Analysis, 2017, 7(2017):244-251.

El Nabarawi MA et al, Formulation, release characteristics, and bioavailability study of gastroretentive floating matrix tablet and floating raft system of Mebeverine HCl, Drug Design, Development and Therapy, 2017, 11:1081-1093.

Shah SH et al, Stomach Specific Floating Drug Delivery System: A Review, International Journal of PharmTech Research, 2009, 1(3):623-633.

Gupta KC and Ravi Kumar MNV, Semi-interpenetrating polymer network beads of crosslinked chitosan-glycine for controlled release of chlorophenramine maleate, Journal of Applied Polymer Science, 2000, 76(5):672-683.

Qadri MF et al, Biomedical Applications of Interpenetrating Polymer Network System, Open Pharmaceutical Sciences Journal, 2015, 2: 21-30.

Sperling LH and Hu R, Interpenetrating Polymer Networks, Polymer Blends Handbook, 2003, 417-447.

Klempner et al, Interpenetrating Polymer Networks, Advances in Chemistry; American Chemical Society, 1994, 21-38,.

Dolas RT et al, Raft Technology for Gatsro Retentive Drug Delivery, Human Journal, 2015, 3(1):232-252.

(56) References Cited

OTHER PUBLICATIONS

Prajapati VD et al, Raft forming system—An upcoming approach of gastroretentive drug delivery system, Journal of Controlled Release, 2013, 168(2):151-165.
Davis SS et al., Transit of Pharmaceutical Dosage Forms Through the Small Intestine, Gut, 1986, 27(8):886-892.
Broughton et al., Gamma-hydroxy-butyrate in the treatment of narcolepsy: a preliminary report, In: Guilleminault et al. (Eds.). Narcolepsy (Advances in sleep research, vol. 3.). Holliswood, NY: Spectrum Publications, pp. 659-667, Jan. 1976.
Flamel Technologies Announces Positive Results of a Second Clinical Trial with Micropump® Sodium Oxybate, Dec. 19, 2014, which reports achieving the objective of one single dose before bedtime.
Frucht et al., A Pilot Tolerability and Efficacy Trial of Sodium Oxybate in Ethanol-Responsive Movement Disorders, Movement Disorders, vol. 20(10):1330-1337, Jun. 2005.
Mamelak et al., The effects of [gamma]-hydroxybutyrate on sleep, Biol Psychiatry, vol. 12(2):273-288, Aug. 1976 (published 1977).
Arora S et al., Floating Drug Delivery Systems: A Review, AAPS PharmScieTech, 2005, 6(3):E372-E390.
Chen Y et al., Cubic and Hexagonal Liquid Crystals as Drug Delivery Systems, BioMed Research International, 2014:1-12.
Jain D et al., Recent technologies in pulsatile drug delivery systems, Biomatter, 2011, 1(1):57-65.
Kumar KK et al., Formulation and evaluation of floating in situ gelling system of losartan potassium, Der Pharmacia Lettre, 2015, 7(1):98-112.
Lam WK et al., Monocarboxylate Transporter-Mediated Transport of Gamma-Hydroxybutyric Acid in Human Intestinal Caco-2 Cells, Drug Metabolism and Disposition, 2010, 38(3):441-447.
Liechti ME et al., Pharmacokinetics and pharmacodynamics of gamma-hydroxybutyrate in healthy subjects, British Journal of Clinical Pharmacology, 2016, 81:980-988.
Madan JR et al., Development and evaluation of in situ gel of pregabalin, International Journal of Pharmaceutical Investigation, 2015, 5(4):226-233.
Patel DM et al., Formulation and Evaluation of Floating Oral In Situ Gelling System of Amoxicillin, ISRN Pharmaceutics, 2011.
Sajan J et al., Chromotherapeutics and Chronotherapeutic Drug Delivery Systems, Tropical Journal of Pharmaceutical Research, 2009, 8(5):467-475.
Vijaya C and Goud KS, Ion-activated In Situ Gelling Ophthalmic Delivery Systems of Azithromyin, Indian Journal of Pharmaceutical Sciences, 2011, 73(6):615-620.
Saito S et al., Combination of borane-dimehtyl sulfide complex with catalytic sodium tetrahydroborate as a selective reducing agent for alpha-hydroxy esters, versatile chiral building block from (s)-(−)-malic acid, Chemistry Letters, 1984, 1984:1389-1392.
International Search Report and Written Opinion dated Apr. 3, 2019 in International Patent Application No. PCT/US2018/066301.
International Search Report and Written Opinion dated Apr. 3, 2019 in International Patent Application No. PCT/US2018/066303.
International Search Report and Written Opinion dated Apr. 15, 2019 in International Patent Application No. PCT/US2018/066300.
International Search Report and Written Opinion dated Apr. 2, 2019 in International Patent Application No. PCT/US2018/066299.
Jain, U.S. Appl. No. 16/955,377, filed Jun. 18, 2020.
Jain, U.S. Appl. No. 16/955,373, filed Jun. 18, 2020.
Jain, U.S. Appl. No. 16/955,392, filed Jun. 18, 2020.
Final Office Action issued on U.S. Appl. No. 16/955,373, dated May 20, 2022.
Jain et al., U.S. Appl. No. 17/725,673, filed Apr. 21, 2022.
Office Action issued in European Patent Application No. 18834152.3, dated Nov. 10, 2022.
Office Action issued in European Patent Application No. 18834153.1, dated Nov. 10, 2022.
Office Action issued in Japanese Patent Application No. 2020-554387, dated Oct. 12, 2022 (translation provided by agent).
Office Action issued in European Patent Application No. 18840118.6, dated Nov. 10, 2022.
Office Action issued in Israeli Patent Application No. 275312, dated Dec. 1, 2022.

GHB PHARMACEUTICAL COMPOSITIONS COMPRISING A FLOATING INTERPENETRATING POLYMER NETWORK FORMING SYSTEM

CROSS-REFERENCE TO RELATED APPLICATIONS

This is a National Stage Entry under 35 U.S.C. 371 of International Patent Application No. PCT/US2018/066300, filed Dec. 18, 2018, which claims priority to U.S. Provisional Patent Application No. 62/607,151, filed Dec. 18, 2017 and U.S. Provisional Patent Application No. 62/728,764, filed Sep. 8, 2018. These applications are incorporated by reference herein.

BACKGROUND OF THE INVENTION

The present invention relates to the field of drug delivery systems.

Interpenetrating polymer networks (IPNs) based on biocompatible and biodegradable materials have been described as a suitable approach for drug delivery where controlled release is desired. An IPN is a combination of at least two polymers, each exhibiting different characteristics. An IPN is formed when at least one polymer network is synthesized or crosslinked independently in the presence of a second other polymer without any covalent bonds forming between them. Typically, an IPN is not formed from normal mixing of two or more polymers.

There are literature reports of different applications of IPNs in the field of drug delivery. IPN based drug delivery systems under development include microspheres, transdermal membranes, sustained release tablets, hydrogel capsules, nanoparticles, sheets for wound dressings, sponges for wound dressings, films, bioengineered tissue, bone substitutes, cartilage scaffolds, calcifiable matrix systems with potential applications in plastic surgery, [Bhardwaj Vineet et al, Interpenetrating Polymer Network (IPN): Novel approach in Drug delivery, International Journal of Drug Development and Research, July-September 2012/Vol 4/Issue 3.]. IPN based drug delivery systems are designed to deliver drugs in zero-order pattern with minimum fluctuation. See, V Bhardway, et al, International J Drug Dev & Research, Vol. 4, Issue 3, July-September 2012.

Gastroretentive drug delivery systems based on floating rafts have been described in the literature. Certain raft systems are floating, which contain a polymer and gas generating agent, designed to delay clearance of the raft system from the stomach. Different raft forming approaches discussed in the prior art include: swelling based raft formation, temperature dependent gelling based raft formation, pH dependent gelling agent based raft formation, ionic cross-linking based raft formation [Pawar Ashish Yashwantrao et al, A Raft forming system: A Novel approach for gastro-retention, Int. J. Pure App. Biosci. 3 (4): 2015 (178-192).] However, Raft formation has been applied in drug delivery field with limited success. Lack of flexibility in tailoring properties so as to impart desired attributes to the resulting raft poses significant limitation on practical applications of current raft forming approaches.

Suitable approaches to raft forming much take into account the gastrointestinal tract physiology. The stomach primarily aims at processing and transporting food. The stomach provides for short term food reservation and quick consumption of relatively large meal. The primary substantial metabolism of enzymes is promoted in stomach of proteins. The peristalsis of stomach mix up and grind consumed food with secretions of the stomach, turning food in simplified liquid form. The liquefied bulk is transported to the small intestine for further digestion. The human anatomy categorizes stomach in three main parts: fundus, body and antrum (pylorus). The proximal portion referred to as fundus and the body functions as storage for undigested food. The antrum provides for the main site for mixing motions and acts as gastric emptying pump by propeller actions. See, Sharma and Khan, Intl J Pharm Sci Res, 2014; Vol 5(4): 1095-1106 The contents of stomach are emptied into duodenum at frequent intervals via a process called gastric emptying. Gastric emptying involves sequence of events (stomach and intestine motility patterns) which are repeated at frequent intervals. Both the fasting and fed states cause gastric emptying. However, the two states are varied upon pattern of motility. Food delays gastric emptying significantly. In this phenomenon, series of electric events takes place in cycles via stomach and intestine every 2 to 3 hours. There occurs a phenomenon of interdigestive myoelectric cycle or migrating myoelectric cycle (MMC), which is divided in 4 phases. The 4 phases are enumerated below (Shailaja pant et al, A Review on Gastroretentive Drug Delivery System, International Journal of Research and Development in Pharmacy and Life Sciences June-July, 2016, Vol. 5, No. 4, pp 2178-2187). More particularly, as described therein, Phase I, the basal phase, lasts from 30 to 60 minutes with rare contractions and is characterized by a lack of secretory, electrical, and contractile activity. Phase II, pre-burst phase, lasts for 20 to 40 minutes with intermittent contractions, during which contractile motions increase in frequency and size. Phase III, burst phase, lasts for 10 to 20 minutes with intense and regular contractions for short period, termed housekeeper waves that sweep off undigested food. Phase IV lasts for 0 to 5 minutes and is the transition period between Phases III and I. Phase III corresponds opening of pyloric valve to fullest To effectively prolong the retention of dosage form in upper GIT, the Raft must possess attributes of floating, swelling, integrity or resiliency and sustained drug release. Floating keeps raft buoyant on biological fluid for longer time periods. Swelling to a size larger than pyloric valve is critical to prevent emptying of raft into duodenum following the gastric emptying process. Raft must possess enough integrity or resiliency to withstand the agitations induced by peristaltic movements and other phases of the interdigestive myoelectric cycle or migrating myoelectric cycle (MMC). While achieving all three attributes, the raft must effectively entrap drug containing particles and provide sustained drug release over targeted period of time. Lack of flexibility in tailoring properties of the raft to achieve desired attributes of swelling, floating, integrity and sustained release poses serious limitation on properties of traditional raft forming approaches. The main reason lies in the fact properties of the raft depend upon the properties of the polymer used for making the raft.

Since there is limitation on number of materials forming the raft, there is limitation on properties/attributes which can be imparted to the raft.

Gamma (γ)-hydroxybutyric acid, is also known as 4-hydroxybutanoic acid. It is commonly used in the form of a salt, which is typically termed gamma hydroxybutyrate. The abbreviation GHB is used in the literature to refer to either the acid or the salt form of the compound.

Initial interest in the use of GHB as a potential treatment for narcolepsy arose from observations made during the use of the sodium salt of GHB for anesthesia. See, WO 2011/

119839. Unlike traditional hypnotics, sodium oxybate is reported to induce sleep that closely resembles normal, physiologic sleep (Mamelak et al., Biol Psych 1977: 12:273-288). It has been reported that early investigators administered GHB to patients suffering from disorders of disturbed sleep, including narcolepsy (Broughton et al. in Narcolepsy, NY, N.Y.: Spectrum Publications, Inc. 1976: 659-668), where it was found to increase total nocturnal sleep time, decrease nocturnal awakenings and increase Stage 3-4 (slow wave) sleep.

XYREM® (sodium oxybate which is a contraction from sodium gamma (γ)-hydroxybutyrate) oral solution has been approved by the US Food and Drug Administration (FDA) for cataplexy and narcolepsy. For optimal clinical effectiveness in narcolepsy, this solution is given twice during the night. For each dose, a measured amount of the oral solution must be removed from the primary container and transferred to a separate container where it is diluted with water before administration. The second dose is prepared at bedtime and stored for administration in the middle of the night. See, XYREM® product literature. XYREM® is marketed by Jazz Pharmaceuticals, Inc., which has several patents covering formulations of gamma-hydroxybutyrate in aqueous media. See, e.g., U.S. Pat. Nos. 8,263,650; 8,324,275, and 8,859,619. The XYREM® product label indicates that the product contains high sodium levels and may not be right for patients on a salt-restricted diet or if patients having high blood pressure, heart failure, or kidney problems. Another drawback associated with the immediate release marketed sodium oxybate product is that the high salt concentration mimics hypertonic solution which may cause vomiting. Removal of sodium from the product could also help improve palatability.

Sodium GHB is highly water-soluble, hygroscopic and strongly alkaline. See, e.g., WO2011/119839. Despite its high-water solubility, it forms a gel when dissolved in water. See, e.g., U.S. Pat. No. 8,193,211, also published as US Patent Application US 2006/0210630 A1. These properties, along with the large amount of the drug that is required to achieve the clinical effect, present challenges in preparing solid unit dosage forms that are designed for immediate release of the sodium GHB into the gastrointestinal tract of the user. See, also, U.S. Pat. No. 8,193,211.

U.S. Pat. No. 8,193,211 describes administration of GHB using pulsed type dosage form, i.e., an immediate release component and a delayed/controlled release component. The immediate release component is described as being an aqueous solution, or a "solid pellet, bead or mini tablet." While the pellets disclosed in Example 1 comprise as much as 80-90 wt % sodium GHB, they are the immediate release portion of the controlled release dosage form and are not formed into a compressed tablet. These immediate release components of GHB are combined with one or more delayed/controlled release components of GHB.

US Patent Publication 2012/0076865 describes a controlled release dosage form for oral administration containing at least one GHB drug, wherein less than 30% of the at least one drug is released during the first hour after administration. The at least one drug is selected from GHB and pharmaceutically acceptable salts, hydrates, tautomers, solvates and complexes thereof.

Flamel has described use of its Micropump®-based technology with sodium GHB for narcolepsy. See, e.g., "Flamel Technologies Announces Positive Results of a Second Clinical Trial with Micropump® Sodium Oxybate", Dec. 19, 2014, which reports achieving the objective of one single dose before bedtime.

The use of drug-ion exchange resin complexes to provide controlled release of active agents has been described. See, e.g., US 2007/0036843 and documents cited therein. This document identifies over 225 possible drugs which may be loaded onto, or bound, to an ion exchange resin, but provides only a couple of working examples. WO2015/166473 reports that ion exchange resin technology is not suitable for many active ingredients.

There continues to be a need for safe, effective and improved patient compliant pharmaceutical formulations for GBH.

SUMMARY OF THE INVENTION

In one aspect, an orally administrable extended release composition which comprises a floating GHB inter-penetrating network (IPN) forming system comprising at least one non-toxic gas generating agent and an IPN forming polymer blend is provided. Suitably, the GHB drug is a gamma hydroxybutyrate or a salt, hydrate, tautomer, solvate, or complex thereof, and/or mixtures of a GHB drug, e.g., mixtures of salts thereof.

In one aspect, the gamma hydroxybutyrate drug composition comprises a floating inter-penetrating network (IPN) forming system. The composition comprises at least one gamma hydroxybutyrate or a salt, hydrate, tautomer, or solvate, or complex thereof as the active pharmaceutical ingredient. The composition further contains a non-toxic gas generating agent and an inter-penetrating network (IPN) forming blend which self-assembles into a floating IPN in situ following oral ingestion. The IPN forming blend comprises (i) at least two polymers which are capable of cross-linking comprising at least one IPN forming anionic polymer and/or at least one IPN forming galactomannan polysaccharide; (ii) at least one cross-linking agent which interacts non-covalently e.g., ionically with the at least two polymers to promote crosslinking in situ, and an optional IPN or a semi-IPN which further cross-links in situ, and one or more optional excipients; wherein following oral ingestion, the composition provides a floating IPN which comprises the polymers individually crosslinked to crosslinking agent/s but not to each other, the gamma hydroxybutyrate drug and the non-toxic gas entrapped therein, thereby providing a floating IPN which controls release of the GHB drug(s). In certain embodiments, the two or more IPN-forming polymers are capable of cross-linking individually to crosslinking agent/s but not to each other via non-covalent bonds, e.g., via ionic bonds. Preferably, the composition is a powder which is reconstituted under conditions which restrict the aqueous component (e.g., water, suspension base, etc.) in order to provide optimal floating IPN properties. In certain embodiments, a product is provided which comprises a GHB floating IPN powder composition for reconstitution in water or an aqueous suspension base comprising a ratio of the (a) powder composition to (b) water of 1:0.1 to 1:15, or 1:0.5 to 1:10, or 1:2 to 1:7. In certain embodiments, the product reconstituted according to these powder:water ratios is a suspension (e.g., at a solid content of less than 20 wt %), a pudding or a paste (e.g., at a solids content of 20 wt % to 50 wt %).

In certain embodiments, the composition self-assembles into a floating IPN in situ following oral ingestion. In certain embodiments, the floating IPN forming system comprises: (i) two or more IPN-forming polymers comprising at least one IPN forming anionic polymer and/or at least one IPN forming galactomannan polysaccharide; (ii) at least one cross-linking agent which interacts with the at least one IPN forming anionic polymer or galactomannan (i) to form an IPN; and (iii) a non-toxic gas generating agent, wherein the gas generating agent forms a non-toxic gas when exposed to stomach acid, wherein following oral ingestion, the composition provides a floating IPN which comprises the at least one moiety and the non-toxic gas entrapped therein, thereby providing a floating IPN. In certain embodiments, the composition IPN forming blend comprises a partially formed IPN or a semi-IPN which further cross-links in situ.

In certain embodiments, a composition is provided in which the floating IPN provides a ratio of $C_{max}$ to plasma concentration for the GHB drug(s) at 5 hours (post dosing) of less than 7, more preferably less than 6; most preferably 1.5 to 5.5, as determined in humans under fasting conditions. In certain embodiments, the composition is taken at least two hours following eating.

In certain embodiments, the orally administrable drug composition comprises: (a) at least one anionic polymer, at least one galactomannan, and at least two cross linking agents; (b) at least two anionic polymers and at least one cross linking agent; (c) at least one galactomannan, at least one anionic polymer, at least one non-ionic polymer and at least two cross linking agents; (d) at least one galactomannan, at least two anionic polymers, at least one non-ionic polymer and at least two cross linking agents; (e) at least two galactomannan polymers and at least one cross linking agent; (f) at least two galactomannan polymers, at least one anionic polymer and at least two cross linking agents; (g) at least two galactomannan polymers, at least one anionic polymer, at least one non-ionic polymer and at least two cross linking agents; (h) at least two galactomannan polymers, at least one non-ionic polymer and at one cross linking agent; (i) at least one anionic polymer, at least one galactomannan, and at least two cross linking agents at least one of which is pH dependent cross-linking agent; ((j) at least one galactomannan, at least one anionic polymer, at least one non-ionic polymer and at least two cross linking agents at least one of which is pH dependent cross-linking agent; (k) at least one galactomannan polysaccharide, at least two anionic polymers, at least one non-ionic polymer and at least two cross linking agents at least one of which is pH dependent cross-linking agent; (1) at least two galactomannan polymers, at least one anionic polymer and at least two cross linking agents at least one of which is pH dependent cross-linking agent; or (m) at least two galactomannan polymers, at least one anionic polymer, at least one non-ionic polymer and at least two cross linking agents at least one of which is pH dependent cross-linking agent.

In certain embodiments, a composition is a tablet, pellet, or capsule. In other embodiments, the composition is a powder. In yet other embodiments, the composition is a powder for suspension (POS). In other embodiments, the composition is a suspension. In yet another embodiment, a composition is a powder to be reconstituted in the form of pudding. In yet another embodiment, a composition is a powder to be reconstituted in the form of paste. In yet another embodiment, composition is powder in sachet supplied along-with suspension base in glass bottle. A powder may be reconstituted using an aqueous suspension base, which comprises the GHB drug, the IPN forming blend, and the at least one gas generating agent, dissolved and/or dispersed therein.

In one aspect, an orally administrable composition is provided which comprises at least one GHB drug and a floating IPN forming system, wherein the IPN forming blend comprises at least one semi-IPN comprising at least one of a cross-linked IPN forming anionic polymer or a crosslinked galactomannan; and at least one cross-linking agent for the at least one IPN forming anionic polymer or galactomannan, wherein following oral ingestion, the semi-IPN is further cross-linked in situ by the cross-linking agent to afford a full-IPN comprising the at least one GHB drug and the non-toxic gas entrapped therein.

In other embodiments, use of a composition as provided herein in treating a subject with a selected GHB drug is provided. In further embodiments, a method for extending the gastric residence and/or release of a GHB drug is provided, which comprises delivering the drug in a composition as provided herein. As described herein, more than GHB drug and/or more than one form of a GHB drug may be in a composition.

In one aspect, an orally administrable composition is provided which comprises at least one GHB drug, at least one non-toxic gas generating agent, and an IPN forming blend, wherein the IPN forming blend comprises: at least one IPN forming anionic polymer or a crosslinked galactomannan; and at least one cross-linking agent for the at least one IPN forming anionic polymer or galactomannan, wherein following oral ingestion, at least one polymer network of the IPN is further cross-linked in situ by the cross-linking agent comprising the at least one moiety compound and non-toxic gas entrapped therein.

In certain embodiments, an orally administrable composition is provided which comprises at least one GHB drug and a floating IPN forming system comprising at least one non-toxic gas generating agent, two or more anionic polymers, and at least one cross-linking agent. In certain embodiments, the composition comprises two or more anionic polymers comprise 10 wt % to 40 wt % of the composition, based on the total dry components (e.g., powder blend). In certain embodiments, the anionic polymers are selected from pectin, gellan gum and/or carrageenan. In certain embodiments, the cross-linking agent(s) comprises about 5 wt % to 15 wt %, or 5 wt % to 12 wt %, or about 11 wt % or 6 wt % to 8 wt %, or about 7 wt % of the composition based on the total dry components (e.g., powder blend). In certain embodiments, the gas generating agent(s) comprises about 5 wt % to about 15 wt %, or about 7 wt % to about 12 wt %, or about 7 wt %, or about 11 wt % of the composition based on the total dry components (e.g., powder blend). In certain embodiments, the gas generating agent is a bicarbonate. In certain embodiments, the bicarbonate is a potassium bicarbonate. In certain embodiments, the remainder of the composition comprises excipients such as diluents, binders, disintegrating agents, and the like.

In certain embodiments, a composition as provided herein comprises an interpenetrating forming blend which comprises an IPN or a semi-IPN which further cross-links in situ.

In a further embodiment, a method of treating a patient having chronic fatigue syndrome, cataplexy, sleep apnea, Parkinson's disease, schizophrenia, binge eating, essential tremor and non-Parkinson's movement disorders, chronic cluster headache, and/or reducing constipation associated with opioids and opioid-related drugs is provided. The method comprises providing said patient with a therapeutically effective amount of a composition as described herein.

In another aspect, a kit for treating a patient with a GHB drug is provided.

Still other aspects and advantages of the invention will be apparent from the following detailed description of the invention.

BRIEF DESCRIPTION OF THE DRAWINGS

FIG. 1A provides an overview of the digestive system, including the stomach, duodenum and jejunum. FIG. 1B provides an enlarged schematic of the stomach, illustrating the entry to the stomach from the esophagus and the exit from the stomach through the pyloric valve into the duodenum. Within the stomach, the floating of the IPN on the gastric fluid is illustrated at different times post-administration, including "floating" and when it "sinks" following drug release in order to clear through the pyloric valve.

DETAILED DESCRIPTION OF THE INVENTION

Figure 1A:
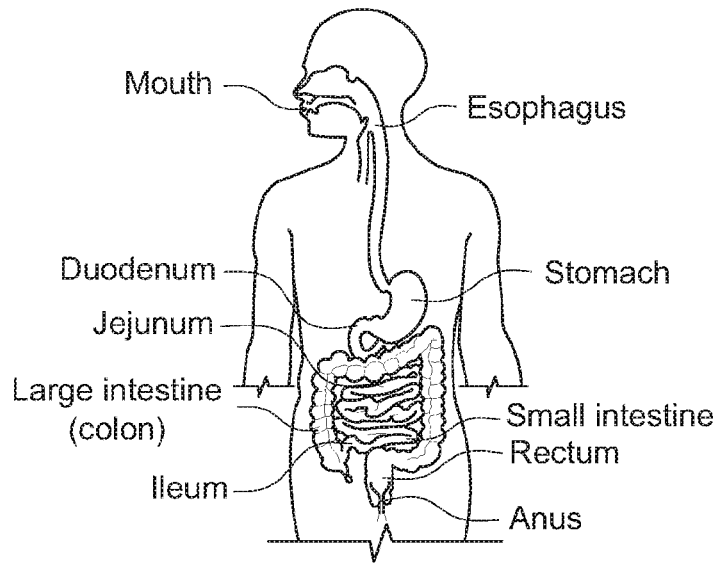
FIGS. 1A and 1B provide schematics of the human gastrointestinal system.

Compositions comprising floating IPN forming systems for delivery of GHB drugs are provided. The compositions are designed to form a floating IPN in situ which controls delivery of the GHB drug(s) entrapped therein. These compositions are particularly useful for retention in the stomach and/or to enhance absorption in the upper gastrointestinal tract (GIT). In certain, the embodiments, the compositions may contain at least one drug-ion exchange resin complex coated with a modified release barrier, at least one IPN forming system, at least one gas generating agent and excipients. The compositions comprising floating IPN forming systems as provided herein can be formulated into a variety of dosage forms including, e.g., tablets, pellets, capsules, powders for suspension (POS) and/or suspensions. These compositions are particularly well suited for extended release compositions.

In one aspect, an orally administrable extended release composition which comprises a floating GHB inter-penetrating network (IPN) forming system comprising at least one non-toxic gas generating agent and an IPN forming polymer blend is provided. Suitably, the GHB drug is a gamma hydroxybutyrate or a salt, hydrate, tautomer, solvate, or complex thereof. Mixtures of a GHB drug, e.g., mixtures of salts thereof. In certain embodiments, the composition contains a GHB-ion exchange resin complex, optionally coated with a modified release coating. In certain embodiments, the composition contains two or more GHB-ion exchange resin complexes which are different (e.g., uncoated and coated, coated with two different coating thicknesses or layers, etc.).

In one aspect, the gamma hydroxybutyrate drug composition comprises a floating inter-penetrating network (IPN) forming system. The composition comprises at least one gamma hydroxybutyrate or a salt, hydrate, tautomer, or solvate, or complex thereof as the active pharmaceutical ingredient. The composition further contains a non-toxic gas generating agent and an inter-penetrating network (IPN) forming blend which self-assembles into a floating IPN in situ following oral ingestion. The IPN forming blend comprises (i) at least two polymers which are capable of crosslinking comprising at least one IPN forming anionic polymer and/or at least one IPN forming galactomannan polysaccharide; (ii) at least one cross-linking agent which interacts non-covalently e.g., ionically with the at least two polymers to promote crosslinking in situ, and an optional IPN or a semi-IPN which further cross-links in situ, and one or more optional excipients; wherein following oral ingestion, the composition provides a floating IPN which comprises the polymers individually crosslinked to crosslinking agent/s but not to each other, the gamma hydroxybutyrate drug and the non-toxic gas entrapped therein, thereby providing a floating IPN which controls release of the GHB drug(s). In certain embodiments, the two or more IPN-forming polymers are capable of cross-linking individually to crosslinking agent/s but not to each other via non-covalent bonds, e.g., via ionic bonds. Preferably, the composition is a powder which is reconstituted under conditions which restrict the aqueous component (e.g., water, suspension base, etc.) in order to provide optimal floating IPN properties. In certain embodiments, a product is provided which comprises a GHB floating IPN powder composition for reconstitution in water or an aqueous suspension base comprising a ratio of the (a) powder composition to (b) water of 1:0.1 to 1:15, or 1:0.5 to 1:10, or 1:2 to 1:7. In certain embodiments, the product reconstituted according to these powder:water ratios is a suspension (e.g., at a solid content of less than 20 wt %), a pudding or a paste (e.g., at a solids content of 20 wt % to 50 wt %).

As used herein "a GHB drug" includes, GHB, as well as pharmaceutically acceptable salts, hydrates, tautomers, solvates, prodrugs and complexes of GHB, and mixtures thereof. Suitable salts of GHB include, e.g., the calcium, lithium, potassium, sodium and magnesium salts. Representative salts are also described in US 2012/0076865, incorporated by reference herein. The sodium salt of GHB, "sodium oxybate", refers to a compound of formula (Ia) below:

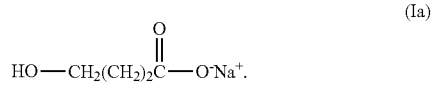

(Ia)

In one embodiment, an alternative to the sodium oxybate may be used as the immediate release component, or as the starting material to prepare a drug-ion exchange resin complex as provided herein. Such alternative salts useful in the present invention include compounds of formula (I):

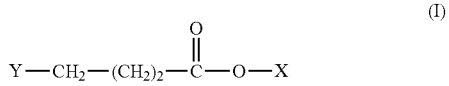

(I)

wherein X is a pharmaceutically-acceptable cation and may be selected from the group consisting of potassium, calcium, lithium and magnesium and Y is OH. By "oxybate salt" is intended a compound of formula I wherein X is a pharmaceutically-acceptable cation and may be selected from the group consisting of sodium, potassium, calcium, lithium and magnesium and Y is OH. Sodium gamma-hydroxybutyrate (GHB) is currently available from Jazz Pharmaceuticals, Inc. as Xyrem® oral solution. Sodium oxybate is a white to off-white, crystalline powder that is very soluble in aqueous solutions. Other salts may be selected, such as calcium oxybate, magnesium oxybate, potassium oxybate, and/or lithium oxybate. Methods of making GHB salts are described, for example, in U.S. Pat. No. 4,393,236, the disclosure of which is incorporated herein by reference.

One exemplary prodrug is 3-hydroxy-γ-butyrolactone. See, e.g., U.S. Pat. No. 6,713,693, which describes a process for preparing enantiomerically pure (S)-3-hydroxy-gamma butyrolactone, the disclosure of which is incorporated by reference herein. (S)-3-hydroxy-γ-butyrolactone can also be obtained from the selective reduction of (L)-malic acid ester (U.S. Pat. No. 5,808,107, the disclosure of which is incorporated by reference herein; Chem. Lett. 1984, 1389).

Such GHB drugs may be in an unaltered state (e.g., free API or a salt thereof) or in the form of a particle, granule, complex, optionally containing excipients, or mixtures thereof. It will be understood that unless otherwise specified, more than one GHB drug may be used in a single composition (e.g., a single dose). By way of non-limited example, a combination of GHB salts may be used rather than a single GHB salt as the "free API"). In certain embodiments, the composition contains another active in addition to the gamma hydroxybutyrate or its salts, hydrates, tautomers, or solvates, or complexes thereof, or mixtures thereof.

In certain embodiments, the GHB drug(s) alone or in combination with at least one additional biologically active moiety is about 0.1 w % to 90 wt %, more preferably about 1 wt % to 75 wt %, or about 15 wt % to 60 wt % based on the total weight of the final dosage form. Unless otherwise specified, when the weight percentage of a complexed GHB or other drug is provided, it is based on the weight of the free base of the drug, unless the pharmaceutically acceptable salt form thereof, is provided. For example, the weight percentage of GHB in a drug-ion exchange resin complex is based on the weight contributed by the GHB, exclusive of any ion exchange resin, polymer, coating, or other component.

A "drug-ion exchange resin complex" refers to the product resulting from loading at least one drug onto an ion exchange resin. In certain embodiments, this describes the complexation which occurs when the active drug(s) and the ion exchange resin are mixed together in an aqueous medium to facilitate the "exchange" between a salt of the drug and the "ion" of the ion exchange resin and the formation of the complex. Unless otherwise specified, a drug-ion exchange resin complex may be uncoated or coated. When in a drug-ion exchange resin complex, a GHB is bound to an anion exchange resin, such as described in more detail below. Other drugs, e.g., modafinil or nalmefene, which may be used in combination or co-therapy with a GHB drug(s) may be bound to a cation exchange resin. In certain embodiments, modafinil may additionally or alternatively complex to an anion exchange resin. Methods for preparing such complexes have been described, e.g., in WO 2007/109104 or US 2007/0215511, incorporated herein by reference. Optionally, a drug-ion exchange resin complex may contain more than one drug bound thereto. Additionally, or alternatively, compositions provided herein, may contain two different drug-ion exchange resin complexes.

Figure 1B:
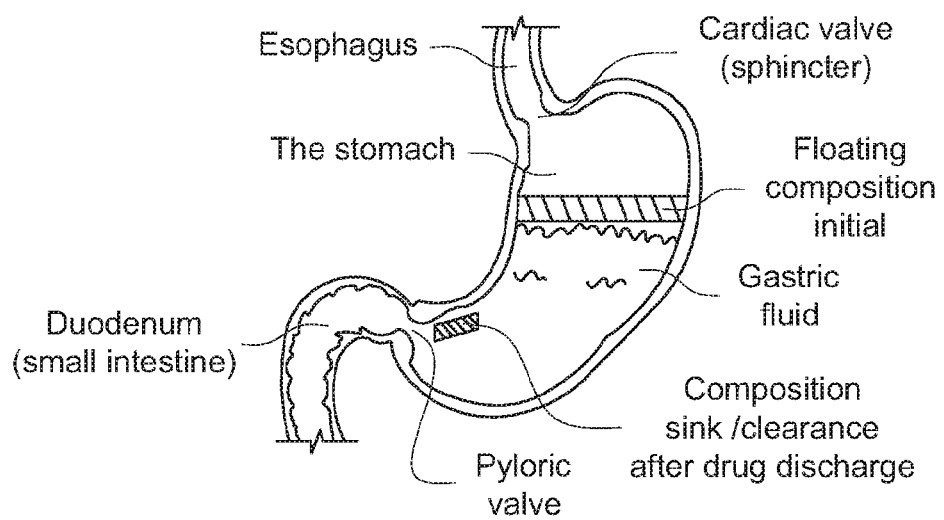

The compositions comprising floating IPN forming systems provide, following dosing, an IPN which floats in acidic pH by entrapping a non-toxic gas into an interpenetrating network. Such non-toxic gas can be generated by gas generating agent after interacting with stomach acid. The present inventors have found that such a floating IPN entraps one or more GHB drugs, oxybate salts, and/or at least one GHB drug-ion exchange resin complexes optionally granulated and/or coated with release retarding agent. In certain embodiments, this provides products containing at least one moiety that exhibits faster and greater absorption in upper part of Gastro-intestinal tract (upper GIT). See, e.g., FIG. 1.

As used in the preceding paragraph and throughout the specification, the "upper part of the GI tract" for absorption includes the stomach, duodenum and jejunum.

Without wishing to be bound by theory, the prolonged retention of the GHB drug(s) in the upper GI tract it is believed this is due to the fact that the floating IPN swell to a size which is larger than the pyloric valve and has a desired integrity/resiliency to withstand agitations induced by peristaltic movement. Further, the floating IPN provide modified drug release profile up from at least 2 hours to up to 24 hours; in certain embodiments, drug release is at least about 3 hours to 24 hours, at least about 6 hours, at least about 8 hours, or at least about 12 hours, or for other desired time periods.

More particularly, the composition comprises: at least one GHB drug; at least one gas generating agent, and an inter-penetrating network (IPN) blend which comprises: (i) at least one IPN forming anionic polymer or at least one IPN forming galactomannan polysaccharide; (ii) at least one cross-linking agent which interacts with the at least one IPN forming anionic polymer or galactomannan (i) to form an IPN, wherein the gas generating agent forms a non-toxic gas when exposed to stomach acid, wherein following oral ingestion, the composition provides a floating IPN which comprises the at least one moiety and the non-toxic gas entrapped therein, thereby providing a floating IPN. In certain embodiments, composition contains one or more different GHB drugs, and/or optionally, another selected drug. Optionally, the an inter-penetrating network (IPN) blend may contain an IPN or a semi-IPN which further cross-links in-situ.

In certain embodiments, a product is an extended release powder for reconstitution comprising (a) a composition comprising the floating IPN forming system and (b) water wherein the ratio, by weight, of the composition to water is 1:0.1 to 1:15, or 1:0.5 to 1:10, or 1:2 to 1:7.

In certain embodiments, a composition is provided in which the floating IPN provides a ratio of $C_{max}$ to plasma concentration for the GHB drug(s) at 5 hours (post dosing) of less than 7, more preferably less than 6; most preferably 1.5 to 5.5, as determined in humans under fasting conditions.

In certain embodiments, the orally administrable GHB drug composition comprises: (a) at least one anionic polymer, at least one galactomannan, and at least two cross linking agents; (b) at least two anionic polymers and at least one cross linking agent; (c) at least one galactomannan, at least one anionic polymer, at least one non-ionic polymer and at least two cross linking agents; (d) at least one galactomannan, at least two anionic polymers, at least one non-ionic polymer and at least two cross linking agents; (e) at least two galactomannan polymers and at least one cross linking agent; (f) at least two galactomannan polymers, at least one anionic polymer and at least two cross linking agents; (g) at least two galactomannan polymers, at least one anionic polymer, at least one non-ionic polymer and at least two cross linking agents; (h) at least two galactomannan polymers, at least one non-ionic polymer and at least one cross linking agent; (i) at least one anionic polymer, at least one galactomannan, and at least two cross linking agents at least one of which is a pH-dependent cross-linking agent; (j) at least one anionic polymer, at least one galactomannan, and at least two cross linking agents at least one of which is pH dependent cross-linking agent; (k) at least one galactomannan, at least one anionic polymer, at least one non-ionic polymer and at least two cross linking agents at least one of which is pH dependent cross-linking agent; (l) at least one galactomannan polysaccharide, at least two anionic polymers, at least one non-ionic polymer and at least two cross linking agents at least one of which is pH dependent cross-linking agent; (m) at least two galactomannan polymers, at least one anionic polymer and at least two cross linking agents at least one of which is pH dependent cross-linking agent; or (n) at least two galactomannan polymers, at least one anionic polymer, at least one non-ionic polymer and at least two cross linking agents at least one of which is pH dependent cross-linking agent.

In one aspect, an orally administrable composition is provided which comprises a floating inter-penetrating network (IPN) forming system formed in situ comprising at least one GHB drug and at least one non-toxic gas generating agent, wherein the composition comprises: (a) at least one GHB drug; (b) at least one semi-IPN comprising at least one of a cross-linked IPN forming anionic polymer or a crosslinked galactomannan; and (ii) at least one cross-linking agent for the at least one IPN forming anionic polymer or galactomannan, wherein following oral ingestion, the semi-IPN is further cross-linked in situ by the cross-linking agent to afford a fully cross-linked floating IPN comprising the at least GHB drug and entrapped non-toxic gas. In certain embodiments, the composition contains two or more different GHB drugs. In certain embodiments, the composition contains at least one GHB drug and, optionally, at least a second, different drug.

In other embodiments, use of a composition as provided herein in treating a subject with a selected drug is provided. In further embodiments, a method for extending the gastric residence and/or release of a drug is provided, which comprises delivering the GHB drug in a composition as provided herein.

In one aspect, an orally administrable composition is provided which comprises a "floating inter-penetrating network (IPN) forming system" comprising at least one non-toxic gas generating agent and an IPN forming polymer blend. The non-toxic gas generating agent produces a gas in the presence of an acid (e.g., stomach acid or an acid of equivalent pH, i.e., a pH of about 1.5 to about 4) to produce a gas. The gas is generated following reaction with the acid and is non-toxic and physiologically compatible. The resulting gas is entrapped within the IPN to afford a floating IPN formed in situ.

This composition comprising a floating IPN forming system provides advantages over the prior art, which utilize polymer blends. By cross-linking the polymers in presence of each other, the resulting floating IPN/semi-IPN having unique properties. Also entrapped within the floating IPN is one or more drugs. The floating IPN provides prolonged gastric retention for these moieties. These features are discussed in more detail below.

As used herein, an "IPN forming blend" or "IPN forming polymer blend" refers to the combination of at least two polymers and at least one cross-linking agent which cross-link to form an IPN in situ, and an optional IPN or a semi-IPN which further cross-links in situ, and one or more optional excipients. Suitably, the composition comprises at least one GHB drug biologically active moiety which is trapped within the floating IPN formed in situ. Preferably, the polymers do not covalently cross-link with each other, but cross-link via the cross-linking agent.

As provided herein, a "floating IPN" comprises a full IPN or a semi-IPN and entrapped gas. Suitably, the floating IPN further contains the active drug(s).

As used herein, a "interpenetrating polymer network (IPN)" comprises two or more polymer networks which are at least partially interlocked on a molecular scale but not covalently bonded to each other and cannot be separated unless chemical bonds are broken. An IPN may be formed sequentially, i.e., in sequential IPN the second polymeric network is formed following the completion of cross-linking of first polymeric network. Alternatively, an IPN may be formed simultaneously, i.e., prepared by a process in which all polymer networks are formed concurrently.

As used herein a "semi IPN" refers to an IPN system wherein less than all of the polymer networks is interlocked on a molecular scale. For example, in an IPN system containing two polymer/polysaccharide components which can be crosslinked, a semi-IPN would reference the system when only one of the two components is crosslinked (networked). For example, in an IPN system containing two crosslinkable polymer/polysaccharide components which can be crosslinked, a semi-IPN would reference the system when only one of the two polymer components is crosslinked (networked). A composition as provided herein, suitable for oral ingestion, may contain a fully crosslinked (full IPN), or a semi IPN.

An IPN may be formed, isolated in-vitro and then used in a composition comprising the GHB drug(s) as provided herein. Additionally, or alternatively, a semi-IPN can be formed first in-vitro. In embodiments in which the composition contains an IPN or a semi-IPN, the composition is designed such that these form further crosslinks upon coming into contact with fluid of upper gastro-intestinal tract (GIT) to form a floating IPN comprising the gas and the GHB drug(s) in situ. IPNs containing anionic polymers are formed by cross-linking using divalent or multivalent cations. Cross-linking of anionic polymers can be achieved in vitro or in vivo or both. When such crosslinking is achieved in-vivo, use of pH sensitive crosslinking agent allows one to achieve floating IPN formation in certain preselected pH range. IPNs containing galactomannan polymers are formed by cross-linking with borax and/or glutaraldehyde. IPNs containing at least one anionic polymer and at least one galactomannan polymers can be formed in vitro but would undergo additional crosslinking with crosslinking agent provide in-situ or in vivo or semi-IPN can be formed in vitro followed by full IPN formation in vivo. IPNs formed completely in-vitro may contain, at a minimum, one non-ionic polymer. A variety of methods for preparing IPN and semi IPN have been described in the literature, including, e.g., casting evaporation, emulsification cross-linking, mini-emulsion/inverse mini-emulsion techniques. See, e.g., Bhardwaj L. et al., African J of Basic & Applied Sciences, Vol. 3 (6), 2011, Pg. 300-312 and Nirmal H. B., et al., Int. J. of PharmTech Research, Vol. 2 (2), 2010, pg. 1398-1408. See, also, J. Lu, et al, Saudi Journal of Biological Sciences, (2016), 23, S22-S31 (available online June 2015); A. Lohani et al, J Drug Delivery, Vol. 2014, pp. 1-11, dx.doi.org/

10.1155/2014/583612; U.S. Pat. Nos. 4,575,539; 5,604,927 (semi-IPN); which are incorporated by reference herein.

In certain embodiments, at least one polymer of semi-IPN or polymer network of IPN formed before administration is further crosslinked in situ with crosslinking agent provided to form floating IPN with at least one moiety and non-toxic gas entrapped therein.

In certain embodiments, two different crosslinking methods are utilized, one for galactomannan and other for anionic polymers and combines both to form full IPN directly or stepwise. For example, for an IPN comprising two galactomannans both of which are crosslinked, the semi-IPN is typically formed prior to being placed in a final product formulation (e.g., during manufacturing) which forms IPN or in situ (e.g., in vivo). In another example, for an IPN comprising one galactomannan and one anionic polymer either anionic polymer or galactomannan may be cross-linked during manufacturing to form semi-IPN and either anionic polymer or galactomannan may be crosslinked in situ to afford floating-IPN with moiety and non-toxic gas entrapped therein. In a further example, for an IPN comprising two anionic polymers, at least one will be cross-linked simultaneously during manufacturing to form semi-IPN and at least one anionic polymer will be crosslinked in situ to afford full-IPN. Alternatively, at least crosslinked network of full-IPN formed during manufacturing would undergo additional crosslinking in situ to afford floating-IPN with moiety and entrapped non-toxic gas. In one embodiment of a stepwise process, galactomannan may be cross-linked during manufacturing and anionic polymer is cross-linked with divalent cations in situ once the cross-linking agent (e.g., crosslinker electrolyte) dissolves in acid (e.g., gastric acid). In an alternative stepwise process, anionic polymer is crosslinked with divalent cations during manufacturing and galactomannan is crosslinked in situ. In another process combining simultaneous and stepwise processes, an IPN comprising one galactomannan and one anionic polymer, both may be crosslinked simultaneously during manufacturing and then additionally crosslinked in situ. In another process combining simultaneous and stepwise processes, IPN comprising two galactomannans both of which are crosslinked during manufacturing and then additionally crosslinked in situ. In another process combining simultaneous and stepwise processes, IPN comprising two anionic polymers both of which are crosslinked during manufacturing and then additionally crosslinked in situ. Certain aspects of the published methods for separately cross-linking of galactomannan or cross-linking of anionic polymers may be applied to the combination provided herein. See, e.g., J. D. Kosmala, D. B. Henthorn, and L. Brannon-Peppas, "Preparation of interpenetrating networks of gelatin and dextran as degradable biomaterials," Biomaterials, vol. 21, no. 20, pp. 2019-2023, 2000; S. S. Bhattacharya, S. Shukla, S. Banerjee, P. Chowdhury, P. Chakrabortyc, and A. Ghosh, "Tailored IPN hydrogel bead of sodium carboxymethyl cellulose and sodium carboxymethyl xanthan gum for controlled delivery of diclofenac sodium," Polymer-Plastics Technology and Engineering, vol. 52, pp. 795-805, 2013; S. Banerjee, G. Chaurasia, D. Pal, A. K. Ghosh, A. Ghosh, and S. Kaity, "Investigation on crosslinking density for development of novel interpenetrating polymer network (IPN) based formulation," Journal of Scientific and Industrial Research, vol. 69, no. 10, pp. 777-784, 2010; K. Landfester, "Synthesis of colloidal particles in miniemulsions," Annual Review of Materials Research, vol. 36, pp. 231-279, 2006. V. Koul, R. Mohamed, D. Kuckling, H.-J. P. Adler, and V. Choudhary, "Interpenetrating polymer network (IPN) nanogels based on gelatin and poly(acrylic acid) by inverse mini-emulsion technique: synthesis and characterization," Colloids and Surfaces B, vol. 83, no. 2, pp. 204-213, 2011. See, also, P. J. Subrahmanyam Design and development of guar gum and borax crosslinked guar gum matrix tablets of theophylline for colon specific drug Journal of Chemical and Pharmaceutical Research, 2012, 4(2):1052-1060; Pawar Ashish Yashwantrao et al, A Raft forming system: A Novel approach for gastro-retention, Int. J. Pure App. Biosci. 3 (4): 2015 (178-192). As provided herein, a "floating IPN" forming system comprises a full IPN or a semi-IPN and a gas generating agent, which produces a gas in the presence of an acid (e.g., stomach acid or an acid of equivalent pH, i.e., a pH of about 1.5 to about 4). The gas generating agent selected is non-toxic and physiologically compatible and produces a gas which is entrapped within the IPN upon interacting with the acid to afford a floating IPN. This composition comprising full IPN or semi-IPN and a gas generating agent is novel and provides advantages over the prior art, many of which utilize polymers which are covalently bound directly to each other. By cross-linking polymers in presence of each other one achieves IPN/semi-IPN having unique properties Also entrapped with in the floating IPN is one or more drugs. The floating IPN provides prolonged gastric retention for these moieties. These features are discussed in more detail below.

Without wishing to be bound by theory, it is believed that following administration, the floating IPN is formed in vivo in less than about 30 minutes, and in certain embodiments, in less than about 20 minutes, and in certain embodiments, in less than about 10 minutes. The onset of floating of a floating IPN may be determined in vitro, using simulated gastric fluid (SGF) and/or another suitable acid. At least one suitable in vitro assay is provided in the examples section herein, and is incorporated by reference herein. Additionally, the floating IPN provided herein may have a duration of floating in vivo of about least 2 hours, and more desirably, at least 3 hours to 24 hours, or about 6 hours to about 12 hours, or about 8 hours to about 10 hours. Duration of floating may be determined through use of an in vitro assay which utilized SGF, such as are described in the examples section and incorporated by reference herein. Additionally, or alternatively, duration of floating of the floating IPN and/or the ability of the IPN to maintain its network may be determined based on the in vitro and/or in vivo release profile of the drug(s) in the composition.

As provided herein, a "gas generating agent" refers to an agent that generates nontoxic gas upon contact with gastric fluid. Suitable gas-generating agents include, without limitation, carbonates or bicarbonates of an alkali or alkaline earth metal, such as potassium carbonate or potassium bicarbonate, sodium carbonate or sodium bicarbonate, calcium carbonate, sodium glycine carbonate, magnesium carbonate, and aluminum carbonate; and sulfites such as sodium sulfite, sodium bisulfite, and sodium metabisulfite. These salts may be used alone or in combination with an acid source as a gas-generating couple. In general, once the gas is entrapped in the floating IPN formed in situ, floating continues as long as integrity of the IPN is retained. Thus, same concentration of gas which works for 3-hour floating is also suitable for longer time periods, e.g., a 12 hr float. In certain embodiments, a gas generating agent is present in concentration range of about 1 w/w to about 25 w/w of the total weight of the floating IPN. Suitably, the gas generating agent provides rapid onset (less than about 15 min) and at least or greater than about 3 hr floating. Float may be assessed in vitro using a suitable assay such as those described herein, e.g., in 500 ml simulated gastric fluid without enzymes, and/or other assays known in the art.

Suitably, the floating IPN provides at least one drug) entrapped therein with a period of retention in the stomach which is longer than the period of time which the moiety would have if administered directly. In certain embodiments, this results in increase bioavailability, absorption, and/or activity in the "gastrointestinal tract" including, the stomach, duodenum, and/or jejunum. "GIT" is an abbreviation for gastrointestinal tract.

As used herein, the term "modified release" refers to release profile of the drug(s) over length of time where the unaltered drug will demonstrate an immediate release profile. Onset of immediate release may be in less than one hour, but release may be delayed, and/or extended, controlled, or sustained over a predetermined period of time. In certain embodiments, this modified release may reflect a period of about 8 hours up to about 24 hours for GHB, more preferably about 3 hours to about 8 hours, more preferably, about 4 hours to about 8 hours, or about 6 hours to about 8 hours, or about 4 hours to about 6 hours. The term "modified release" may include, e.g., composition which are extended release formulations, controlled release formulations, sustained release formulations, and/or delay release formulations. In certain embodiments, a floating IPN of the invention may be used in conjunction with a delayed release component, such as, e.g., the novel trigger pulse system Raft system described in the co-pending US provisional patent application entitled "Pharmaceutical Composition Comprising GHB Gastro-Retentive Raft Forming Systems Having Trigger Pulse Drug Release", filed on the same date herewith.

"Extended release" refers to the release profile of the active moiety over an extended period of time, e.g. over a period of at least 2 hours, and more desirably, at least about 3, about 4, about 6, about 8, about 10, about 12, about 16, about 20 or about 24 hours. The term "immediate release" ("IR") refers to the release of a drug from a pharmaceutical formulation where the rate of release of the active pharmaceutical ingredient from the pharmaceutical formulation is not substantially retarded by means of a controlled release matrix or other such means and where the components of the pharmaceutical formulation are designed such that, upon ingestion, maximum exposure of said active pharmaceutical ingredient to body tissues occurs in the minimum period of time. As described herein, an "immediate release" component releases about 100% in less than 1 hour.

Components of IPN and IPN Forming Systems

In the following discussion, it should be understood that the IPN forming blend described herein may be included in an oral composition as separate polymers, a semi IPN (which may form fully networked IPN in situ (in vivo)), or a previously formed IPN which further cross-links to form a floating IPN in situ, wherein at least one polymer network of the IPN is further crosslinked in situ with a crosslinking agent provided. The floating IPN provided herein are characterized by rapid onset (e.g., less than about 15 min) and a sufficient amount of gas to provide a duration of floating of at least about >3 hr, more preferably at least 6 hr, more preferably about 12 hr) when assessed in vitro, e.g., in 500 ml simulated gastric fluid (SGF) without enzyme. In addition, the dosage form based on floating IPN is characterized by having enough strength to be able to retain integrity for the desired period of time, e.g., at least for a period about at least about 3 hours, more preferably for at least about 6 hr, more preferably about 12 hr when assessed in vitro, e.g., in 500 ml SGF without enzyme agitated using mechanical shaker set at 37° C. and 75 rpm. Within these parameters, the following components are not limiting, as other IPN forming components may be included in the composition.

a. Anionic Polymers and Crosslinking Agents

One or more anionic polymers may be used to form an IPN or semi-IPN, optionally in combination with galactomannan and/or another polymer, e.g., a non-ionic polymer. Such anionic polymers may include, without limitation, at least of each pectins, alginic acid, gellan gum, carrageenan, xanthan gum, and/or combinations thereof. In certain embodiments, pectins are included. Pectins have a polymer backbone which mainly comprises α-(1-4)-D galacturonic acid residues. Free calcium ions, which crosslink the galacturonic acid chains. A source of divalent ions, generally calcium ions is required to produce vehicles for drug delivery. The main advantage of using pectin for these formulations is that it is water soluble, so organic solvents are not necessary in the formulation. Calcium ions in the complexed form may be included in the formulation for the induction of pectin cross-linking. In other embodiments, alginic acid is included. Alginic acid is a linear block copolymer polysaccharide consisting of β-D-mannuronic acid and α-L-glucuronic acid residues joined by 1,4-glycosidic linkages. Dilute aqueous solutions of alginates undergo crosslinking with di and trivalent metal ions by a cooperative process involving consecutive glucuronic residues in the α-L-glucuronic acid blocks of the alginate chain. Alginic acid can be chosen as a vehicle for formulations, since it exhibits favorable biological properties such as biodegradability and nontoxicity. Gellan gum (commercially available as Gelrite™ or Kelcogel™) is an anionic deacetylated exocellular polysaccharide secreted by *Pseudomonas elodea* with a tetrasaccharide repeating unit of one α-L-rhamnose, one β-D-glucuronic acid and two β-D-glucuronic acid residues. Chemical structure of the polysaccharide has a tetrasaccharide repeat unit consisting of two glucose (Glc) residues, one glucuronic acid (GlcA) residue, and one rhamnose (Rha) residue. Similar to alginic acid and pectin, gellan gum chains are crosslinked by divalent or trivalent metal ions. Carrageenans are a family of linear sulfated polysaccharides that are extracted from red edible seaweeds. There are three main varieties of carrageenan, which differ in their degree of sulphation. Kappa-carrageenan has one sulphate group per disaccharide, Iota-carrageenan has two, and Lambda-carrageenan has three. Iota carrageenan is cross linked by divalent cations while kappa carrageenan is crosslinked by monovalent cations. Xanthan gum is anionic polysaccharide composed of pentasaccharide repeat units, comprising glucose, mannose, and glucuronic acid in the molar ratio 2:2:1.

In certain embodiments, an IPN forming system comprises about 3% w/w to about 30% w/w of one or more anionic polymer(s), or about 3% w/w to about 20% w/w, or about 3% w/w to about 15% w/w, or about 3% w/w to about 10% w/w, or about 5%, or about 10%, or about 5% w/w to about 30% w/w, or about 10% w/w to about 30% w/w, or about 15% w/w to about 25% w/w.

One or more cross-linking agents suitable for anionic polymers may be selected from the following non-limiting list of divalent and trivalent metal salts: Calcium salts such as, e.g., calcium carbonate, calcium chloride, calcium gluconate; magnesium salts, ferrous salts, ferric salts, aluminum salts, zinc salts, or combinations thereof. In certain embodiments, the cross-linking agents can be the counter ions coming from the excipients and/or the active agents. In other embodiments, cross-linking metal ions might be provided by crosslinking agent in the composition or such metal ion might be provided by mono- or di- or polyvalent metal ion salt forms of moiety. Otherwise, such crosslinking metal ion may be provided by an excipients. For example, calcium carbonate can be used as gas generating agent but it also provides calcium ions for crosslinking anionic polymers including pectin, carrageenan iota, gellan gum, xanthan gum and the like. In certain embodiments, an IPN forming system comprises about 2% w/w to about 15% w/w of the anionic polymer(s) cross-linking agent(s), or about 2% w/w to about 10% w/w, or about 2% w/w to about 5% w/w, or about 5%, or about 7%, or about 5% w/w to about 15% w/w, or about 10% w/w to about 15% w/w.

b. Galactomannan Polysaccharides and Crosslinking Agents

Galactomannans are polysaccharides consisting of a mannose backbone with galactose side groups (more specifically, a (1-4)-linked beta-D-mannopyranose backbone with branch-points from their 6-positions linked to alpha-D-galactose, i.e. 1-6-linked alpha-D-galactopyranose). Examples of suitable galactomannans include, in order of increasing number of mannose-to-galactose ratio: fenugreek gum, mannose:galactose ~1:1; guar gum, mannose:galactose ~2:1; tara gum, mannose:galactose ~3:1; locust bean gum or carob gum, mannose:galactose ~4:1. Combinations of galactomannans may be utilized in the IPN forming systems (e.g., the floating IPN forming system and the IPN forming blend) provided herein. These are not limitations on the galactomannans which are useful and which may be obtained from a variety of sources, including those identified below.

In certain embodiments, the IPN forming systems comprise about 3% w/w to about 30% w/w of galactomannan(s), or about 3% w/w to about 20% w/w, or about 3% w/w to about 15% w/w, or about 3% w/w to about 10% w/w, or about 5%, or about 10%, or about 5% w/w to about 30% w/w, or about 10% w/w to about 30% w/w, or about 15% w/w to about 25% w/w.

TABLE 1

Galactomannans of Leguminosae species

| Botanical name | | |
|---|---|---|
| Subfamily | Species | M/G ratio |
| CAESALPINIACAE | Cassia absus | 3.00 |
| | C. emarginata | 2.70 |
| | C. Fistula | 3.00 |
| | C. leptocarpa | 3.05 |
| | C. marylandica | 3.76 |
| | C. nodosa | 2.7-3.5 |
| | C. occidentalis | 3.00 |
| | C. tora | 3.00 |
| | Ceratonia siliqua | 3.75 |
| | Caesalpinia cacalaco | 2.50 |
| | C. pulcherima | 2.7 |
| | C. spinosa | — |
| | Cercidium torreyanum | 3.38 |
| | Delonix regia | 4.28 |
| | Gleditsia amorphoides | 2.5 |
| | G. triacanthos | 3.2 |
| | Gymnocladus dioica | 2.71 |
| | Parkinsonia aculeata | 2.70 |
| MIMOSACEAE | Besmanthus illinoensis | 2.89 |
| | Leucaena galauca | 1.33 |
| FABACEAE | Sophora japonica | 5.19 |
| | Genista raetam | 4.14 |
| | G. scoparia | 1.69 |
| | G. cretica | 1.56-167 |
| | G. foenum-graecum | 1.2 |
| | G. hamosa | 1.17 |
| | G. monspeliaca | 1.08 |
| | G. polyserata | 1.13 |

TABLE 1-continued

Galactomannans of Leguminosae species

| Botanical name | | |
|---|---|---|
| Subfamily | Species | M/G ratio |
| | G. radiata | 1.17 |
| | Anthyllis vulneraria | 1.33 |
| | Lotus corniculatus | 1.25 |
| | L. pedunculatus | 1.04 |
| | L. scoparius | 1.13 |
| | Alysicarpus veginalis | 1.14 |
| | Desmodium pulchellum | 2.00 |

TABLE 2

Galactomannans of non-leguminous plants

| Botanical name | | |
|---|---|---|
| | | M/G ratio |
| ANNONACEAE | Annona muricata | 4.46 |
| CONVOLVULACEAE | Convolvulus tricolor | 1.75 |
| | Ipomoea muricata | 1.8 |
| EBENACEAE | Diospyros virginiana | — |
| LOGANIACEAE | Strychnos nux-vomica | — |
| PALMAE | Borassus flabellifer | 2.4 |
| | Cocos mucifera | 2.57 |
| | Arenga saccharifera | 2.26 |
| | Phytelephas macrocarpa | 50 |
| | Hyphaene thebaica | 19 |
| | Phoenix dactylifera | 10 |

Suitable cross-linking agent for use with a galactomannan may selected from the following non-limiting list: borax, glutaraldehyde, boric acid, organotitanates, other organometallic crosslinkers including Zr, Al, Cr, or combinations thereof.

In certain embodiments, an IPN forming system comprises about 2% w/w to about 15% w/w of the galactomannan(s) cross-linking agent(s), or about 2% w/w to about 10% w/w, or about 2% w/w to about 5% w/w, or about 5%, or about 7%, or about 5% w/w to about 15% w/w, or about 10% w/w to about 15% w/w.

c. Non-Ionic Polymers as Components of IPN

Selected from non-limiting list of non-ionic polymers: cellulose polymers and their derivatives (such as for example, hydroxyethylcellulose, hydroxypropylcellulose, hydroxypropyl methyl cellulose, methyl cellulose), polysaccharides and their derivatives, polyalkylene oxides, polyethylene glycols, xyloglucan.

In certain embodiments, non-ionic polymers may be present in the floating IPN forming systems provided herein in an amount of about 2% w/w to about 15% w/w of the IPN forming system, or about 2% w/w to about 10% w/w, or about 2% w/w to about 5% w/w, or about 5%, or about 7%, or about 5% w/w to about 15% w/w, or about 10% w/w to about 15% w/w. However, higher or lower amounts of such polymers may be selected as needed or desired.

d. Liquid Crystals Formers as Optional Components of IPN

In addition to an anionic polymer and/or galactomannan component, liquid crystal forms may be included in an IPN. The cubic phases are used as the carriers for hydrophilic, lipophilic, or amphiphilic drugs. The hexagonal phase is composed of cylindrical micelles packed in a hexagonal pattern. In contrast to the cubic phase, the water channels in the hexagonal phase are closed. The distribution of drugs in hexagonal phase is similar to that in cubic phase. Cubic and hexagonal phases provide a slow drug release matrix and protect peptides, proteins, and nucleic acids from chemical and physical degradation.

Suitable Cubic Phase-Forming Lipids may include, e.g., Glyceryl monooleate (GMO, 2,3-dihydroxypropyl oleate), phytantriol (PT, 3,7,11,15-tetramethyl-1,2,3-hexadecanetriol) and other lipids such as monolinolein, monoelaidin, phosphatidylethanolamine, oleoylethanolamide, phospholipids, PEGylated phospholipids, alkyl glycerates, and glycolipids have been reported to form cubic phase. Suitable hexagonal Phase-Forming Lipids may include, e.g., Oleyl glycerate (OG,2,3-dihydroxypropionic acid octadec-9-enyl ester) and phytanyl glycerate (PG, 2,3-dihydroxypropionic acid 3,7,11,15-tetramethyl-hexadecyl ester) are found to form hexagonal phase at physiological temperature when exposed to excess water, which further expands the lipid pool to form hexagonal phases.

In certain embodiments, liquid crystal formers may be present in the floating IPN forming systems provided herein in an amount of about 2% w/w to about 15% w/w of the IPN forming system, or about 2% w/w to about 10% w/w, or about 2% w/w to about 5% w/w, or about 5%, or about 7%, or about 5% w/w to about 15% w/w, or about 10% w/w to about 15% w/w. However, higher or lower amounts of liquid crystal formers may be selected as needed or desired.

e. Illustrative Floating IPN Forming Systems

As provided herein, orally pharmaceutical compositions (final dosage forms) are provided which contain a floating IPN forming system, composed of at least one GHB drug, at least one gas generating agent, and an IPN forming blend containing at least one crosslinking agent and two IPN forming polymers (optionally already in the form of a semi IPN or full IPN). In certain embodiments, when the composition contains a floating IPN forming system comprising IPN forming blend, having two or more polymers which are optionally in the form of a semi IPN or a formed IPN which is further crosslinkable). The floating IPN formation is completed in vivo such that the floating IPN contains a full IPN comprising the gas generated and at least one GHB drug. In certain embodiments, the composition contains a floating IPN forming system, composed of an IPN and a crosslinking agent for additional crosslinking of at least one of the polymer networks of the IPN. Such that following administration, the floating IPN is formed in situ along with the gas which is entrapped to forms the floating IPN in situ (in vivo). Optionally such systems may include a liquid crystal IPN.

In certain embodiments, the IPN forming blend comprises at least one anionic polymer, at least one galactomannan and at least two cross-linking agents. In certain embodiments, the floating IPN forming system comprises carrageenan iota (anionic polymer), guar gum (galactomannan), borax (crosslinking agent) and calcium carbonate (crosslinking agent).

In certain embodiments, the IPN forming blend comprises at least two anionic polymers and at least one cross-linking agent. In certain embodiments, the IPN forming blend comprises carrageenan iota (anionic polymer), pectin (anionic polymer) and calcium carbonate (crosslinking agent).

In certain embodiments, the IPN forming blend comprises at least one galactomannan, at least one anionic polymer, at least one non-ionic polymer and at least two cross-linking agents. In certain embodiments, the IPN forming blend comprises guar gum (galactomannan), carrageenan kappa (anionic polymer), HPMC K100M (non-ionic polymer), borax (crosslinking agent) and potassium citrate (crosslinking agent).

In certain embodiments, the IPN forming blend comprises at least one galactomannan, at least two anionic polymers, at least one non-ionic polymer and at least two cross-linking agents. In certain embodiments, the IPN forming blend comprises fenugreek gum (galactomannan), carrageenan iota (anionic polymer), pectin (anionic polymer), HPMC K100M (non-ionic polymer), borax (crosslinking agent) and calcium carbonate (crosslinking agent).

In certain embodiments, the IPN forming blend comprises at least two galactomannan polymers, at least one gas generating agent, and at least one cross-linking agent. In certain embodiments, the IPN forming blend comprises fenugreek gum (galactomannan), guar gum (galactomannan), calcium carbonate and borax (crosslinking agent).

In certain embodiments, the IPN forming blend comprises at least two galactomannan polymers, at least one anionic polymer and at least two cross-linking agents. In certain embodiments, the IPN forming blend comprises fenugreek gum (galactomannan), guar gum (galactomannan), pectin (anionic polymer), calcium carbonate (crosslinking agent) and borax (crosslinking agent).

In certain embodiments, the IPN forming blend comprises at least two galactomannan polymers, at least one anionic polymer, at least one non-ionic polymer and at least two cross-linking agents. In certain embodiments, the IPN forming blend comprises fenugreek gum (galactomannan), guar gum (galactomannan), carrageenan iota (anionic polymer), HPMC K100M (non-ionic polymer), calcium carbonate (crosslinking agent) and borax (crosslinking agent).

In certain embodiments, the IPN forming blend comprises at least two galactomannan polymers, at least one non-ionic polymer and at least one cross-linking agent. In certain embodiments, the IPN forming blend comprises fenugreek gum (galactomannan), guar gum (galactomannan), HPMC K100M (non-ionic polymer) and calcium carbonate (crosslinking agent).

Components of Composition

In addition to the floating IPN forming system which includes the gas generating agent(s) and IPN forming blend as described above, the compositions provided herein include, at a minimum, at least one GHB drug, pharmaceutically acceptable excipients. The GHB drug may be included in the composition in an uncomplexed form (e.g., as a free GHB or as an oxybate salt), or may be prepared in a granule, particle, complex (e.g., drug-ion exchange resin complex). These various forms of the drug(s) may be uncoated or provided with one or more modified release coating. In certain embodiments, the compositions contain, in addition to the at least one GHB drug, one or more additional different drugs and/or other moieties. In certain embodiments, the compositions may contain the same moiety in two or more different forms (e.g., uncoated and modified release coated, two different immediate release forms, an immediate release and a modified release, two different modified release forms, or combinations thereof). Various combinations of the same drugs in different forms and/or different GHB with other drugs in the same or different forms is permitted. Examples of suitable doses of a drug(s) which could be incorporated into the floating IPN may be in the range of about 0.01 mg to 15 gm, or ranges or values therebetween. In certain embodiments, a lower dose of a selected drug may be delivered via the floating IPN. In certain embodiments, the dose is from about 100 mg (0.1 gram) to about 12 grams, or 1.25 grams to 9 grams of the GHB drug, or 4 grams, 4.5 grams, 6 grams, or 7.5 grams as based on equivalence to sodium oxybate. In other embodiments, higher or lower amounts may be included in the composition.

In certain embodiments, a single composition may contain a first floating IPN-forming systems comprising at least one GHB drug and at least a second floating IPN-forming system comprising a different drug for co-delivery with the GHB drug. In certain embodiments, a composition contains a powder of IPN-forming systems comprising at least one GHB drug and at least a second, non-GHB drug for co-delivery with the GHB drug. In certain embodiments, the composition is powder. In other embodiments, the composition is a paste or suspension reconstituted from a powder.

In certain embodiments, modafinil is co-delivered, e.g., in an amount of about 200 mg to about 600 mg per day. In other embodiments, armodafinil is co-delivered, e.g., in an amount of 150 mg to 250 mg. In certain embodiments, pitolisant is co-delivered, e.g., in an amount of 5 mg to 40 mg per day. In certain embodiments, oxybate may be co-administered with a stimulant or SSRI. Suitable drugs for GHB drug co-delivery may be, e.g., amphetamine (e.g., in an amount of about 10 mg to about 30 mg per day), methylphenidate (e.g., in an amount of about 5 mg to about 20 mg per day), or fluoxetine (e.g., about 10 mg to about 40 mg per day).

Biologically Active/Useful Moieties

Regardless of the form in which they are to be incorporated in the floating IPN forming system and floating IPN, the selected GHB drugs or their particles, granules, complexes, etc., selected for inclusion in the floating IPN forming system and floating IPN have an average size of less than about 500 microns in size, preferably less than about 425 microns. However, the various GHB components (particles, granules, complexes, etc.) having a larger size may be selected depending upon the total weight (dose) being delivered and/or by adjusting the amount of gas generating agent. In certain embodiments, the composition of the invention includes, in additional to the GHB drug, a second biologically active moiety which is useful in a combination or in a co-therapy with the GHB drug. For example, such a drug may be modafinil (e.g., for treating narcolepsy), nalmefene (e.g., for use in treating alcohol dependency or abuse) and may be administered in immediate release or modified release form, within the floating IPN, in the composition but outside of the floating IPN, or administered by a different route as a co-therapy. These or another drug(s) for use in combination or co-therapy with the GHB drug of the composition is selected is one which, when administered outside of the composition of the invention, has more rapid clearance from the stomach and, optionally other parts of the gastrointestinal tract than is desired. Thus, the composition of the invention can provide a modified release profile to a drug and increased bioavailability. This is particularly desirable for drugs which are to be targeted to the gastrointestinal tract (particularly the stomach). However, this is not a limitation on its utility.

A composition as provided herein contains, at a minimum, at least one GHB drug which may be an uncomplexed GHB salt, and/or at least one drug-ion exchange resin complex containing GHB. In certain embodiments, a composition as provided herein is a combination product containing at least one GHB drug and a second, different, drug, e.g., modafinil, nalmefene, or another suitable drug. Typically, formation of a drug-ion exchange resin complex involves exchanging the acid or base salt of the compound (e.g., a drug) with the counterion from an ion exchange resin. However, zwitterionic or non-salt forms of certain drugs may form a complex with an ion exchange resin complex. Such complexes may contain one or more drugs. In certain embodiments, two or more drug-ion exchange resin complexes having different drugs may be used in a single composition. In certain embodiments, two or more drug-ion exchange resin complexes which are in different release forms, e.g., immediate release, modified release, including different modified release coatings, may be used in a single composition.

Methods of complexing drugs with ion exchange resins is known in the art. For example, suitable methods for preparing such complexes and examples of suitable ion exchange resins are described in U.S. Pat. Nos. 8,062,667, 8,287,848, 8,202,542, which are incorporated herein by reference. See, also, US 2007/0148239A1; WO 2007/001300; U.S. Pat. No. 4,352,891, and K. Hanninen, et al, Eur J Pharm Sci., 31 (2007): 306-317. Ion exchange resins suitable for pharmaceutical use are typically water-insoluble and comprise a preferably pharmacologically inert organic and/or inorganic matrix containing functional groups that are ionic or capable of being ionized under the appropriate conditions of pH, in order to permit ion exchange with the drug (other moiety) being complexed therewith. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion exchangers suitable for use in ion-exchange chromatography and for such applications as deionization of water are suitable for use in the controlled release of drug preparations. Such ion-exchangers are described by H. F. Walton in "Principles of Ion Exchange" (pp: 312-343) and "Techniques and Applications of Ion-Exchange Chromatography" (pp: 344-361) in Chromatography. (E. Heftmann, editor), van Nostrand Reinhold Company, New York (1975). Ion exchange resins that can be used in the present invention have exchange capacities of about 6 milliequivalents (meq)/gram and preferably about 5.5 meq/gram or below. Typically the size of the ion-exchange particles is from about 5 microns to about 750 microns, preferably the particle size is within the range of about 40 microns to about 250 microns for liquid dosage forms although particles up to about 1,000 micron can be used for solid dosage forms, e.g., tablets, pellets, powders (including powders for suspensions), and capsules. Particle sizes substantially below the lower limit are generally difficult to handle in all steps of the processing. Generally, uncoated drug-ion exchange resin particles will tend to be at the lower end of this range, whereas coated drug-ion exchange resin particles will tend to be at the higher end of this range. However, both uncoated and coated drug-ion exchange resin particles may be designed within this size range.

The most common organic resins used in formulations are cross-linked polystyrene and polymethacrylate polymers. Ion exchange resins are broadly classified into two main categories, as cation exchange resins and anion exchange resins. Cation exchange resins contain anions attached to polymer and active cations. Cation exchange resins are prepared by the copolymerization of styrene and divinyl benzene and have sulfonic acid groups ($—SO_3H$) introduced into most of the benzene rings. Strong cation acid resins are so named because their chemical behavior is similar to that of a strong acid. These resins are highly ionized in both the acid (R—SO$_3$H) and salt (RSO$_3$Na) form of the sulfonic acid group (—SO$_3$H). The hydrogen and sodium forms of strong acid resins are highly dissociated, and the exchangeable Na$^+$ and H$^+$ are readily available for exchange over the entire pH range. Consequently, the exchange capacity of strong acid resins is independent of the solution pH. For example, sodium polystyrene sulfonate USP (Amberlite IRP 69). Weak Acid Cation Exchange Resins: These resins behave similarly to weak organic acids that are weakly dissociated. In a weak acid resin the ionizable group is a carboxylic acid (COOH) as opposed to the sulfonic acid group (SO$_3$H) used in strong acid resins. The degree of dissociation of a weak acid resin is strongly influenced by the solution pH. Consequently, resin capacity depends in part on the solution pH. A typical weak acid resin has limited capacity below a pH of 6.0.

Anion exchange resins can be prepared by first chloromethylating the benzene rings of styrene-divinylbenzene copolymer to attach CH$_2$Cl groups and then causing these to react with tertiary amines such as triethylamine. A strong base type anion exchange resin is highly ionized and exchange capacity is not affected by pH. In certain embodiments, a strongly basic anion exchanger contains quaternary ammonium groups attached to a styrene and divinylbenzene copolymer. An example of strong base anion exchange resin is cholestyramine. Duolite AP143/1083 is cholestyramine USP supplied by Dow Chemical Company. A weak base type anion exchange resins exhibit minimal exchange capacity above pH 7. An example of a weakly basic anion exchangers contain polyalkylamine groups attached to a styrene and divinyl benzene.

Inorganic ion exchangers include zeolites, which are microporous, aluminosilicate minerals. Zeolites have a porous structure that can accommodate a wide variety of cations, such as Na+, K+, Ca2+, Mg2+ and others. These positive ions are rather loosely held and can readily be exchanged for others in a contact solution. Some of the more common mineral zeolites are analcime, chabazite, clinoptilolite, heulandite, natrolite, phillipsite, and stilbite. An example of the mineral formula of a zeolite is: Na$_2$Al$_2$Si$_3$O10.2H$_2$O, the formula for natrolite.

The selected ion-exchange resins may be further treated by the manufacturer or the purchaser to maximize the safety for pharmaceutical use or for improved performance of the compositions. Impurities present in the resins may be removed or neutralized by the use of common chelating agents, anti-oxidants, preservatives such as disodium edetate, sodium bisulfite, and so on by incorporating them at any stage of preparation either before complexation or during complexation or thereafter. These impurities along with their chelating agent to which they have bound may be removed before further treatment of the ion exchange resin with a granulating agent and optional modified release coating.

Binding of the selected drug or combination of drugs to the ion exchange resin can be accomplished using methods known in the art. The binding may be performed, for example as a batch or column process, as is known in the art. Typically the drug-ion exchange resin complex thus formed is collected by filtration and washed with appropriate solvents to remove any unbound drug or by-products. The complexes can be air-dried in trays, in a fluid bed dryer, or other suitable dryer, at room temperature or at elevated temperature.

In one example, drug-ion exchange resin complex can be prepared by dissolving the drug(s) in deionized water, adding ion exchange resin USP under stirring and continuing stirring further. The stirring is continued further for a period of 15 min to 20 hrs. More preferably, for 30 min to 10 hr, more preferably from 1 hr to 5 hr. In one embodiment, the drug-ion exchange resin complexes can be prepared using methods known in the art, such as, but not limited to, blending, slurrying, kneading, grinding, sieving, filling, compressing, lyophilization, spray-drying, fluid-bed drying or centrifugal granulation. The drug-resin binding may be performed, for example, as a batch or column process, as is known in the art. In one illustrative embodiment, drug-resin complex is prepared by batch process. In one embodiment the drug-resin complexes were prepared by stirring aqueous slurry of drug and ion exchange resin for about 0.5 hours to about 12 hours, followed by filtration and drying of the formed drug-resin complex. Drug: ion exchange resin by weight ratio in the complex (also termed a resinate) can be from 1:0.1 to 1:100, more preferably from 1:1 to 1:10. The amount of drug that can be loaded onto a resin will typically range from about 1% to about 75% w/w of the drug-ion exchange resin particles. In one embodiment, loading of about 10% to about 40% w/w, more desirably, about 15% to about 30% w/w, of the drug-ion exchange resin particles can be employed. Typical loadings of about 25 w/w of the drug-ion exchange resin particles can be advantageously employed.

Optionally, a drug-ion exchange resin complex may be granulated with a polymer in preparation for formulation and/or for further processing (e.g., coating). Such a polymer may optionally provide modified release properties to the drug(s) in the complex. Suitably, the granulating agent does not form a separate coating layer on the drug-ion exchange resin complex, but forms a matrix therewith. Examples of suitable polymer systems include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems. One suitable polymer system which may provide release retardant properties is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; although less desirable, certain pH-dependent members of the EUDRAGIT polymer family, e.g., the L, S, and E, polymers may be selected. Examples of polymers and/or polymer systems which do not provide any significant release retardant properties include the impregnating agents described for example in U.S. Pat. No. 4,221,778 and published US Patent Application Publication No. US 2003/009971 A1, the disclosures of which are incorporated herein by reference. Specific examples of suitable impregnating agents include propylene glycol, polyethylene glycol, polyvinyl alcohol, polyvinyl pyrrolidone (e.g., KOLLIDON® K30) mannitol, methyl cellulose, hydroxypropyl methylcellulose, hydroxypropyl cellulose, and sorbitol. The quantity of the granulating agent typically ranges from about 3% w/w to about 30% w/w or more by weight of the uncoated drug-ion exchange resin particles. The granulating agent, if used, is generally in the range from about 5% w/w to about 20% w/w, or about 10% w/w to about 15% w/w of the uncoated drug-ion exchange resin complex. These granulating agents can be added during the formation of the drug-ion exchange resin complex either in the beginning, during the middle, or after substantial amount of complex formation has taken place. In the more preferred embodiment, the retardant is added after the formation of drug-ion exchange resin complex. Upon admixing, the drug-ion exchange resin complex particles with the granulating agent, the mixture is dried and milled appropriately. In some cases, the milling may be carried out before the complete drying of the complex and then again further drying followed by milling to obtain the desired size or other desired characteristics.

The drug-ion exchange resin complexes (optionally in a matrix with at least one granulating agent) may be coated with at least one modified release coating. Optionally, the drug-ion exchange resin complex may have two or more different modified release coatings. These coatings may be pH-dependent (such as enteric or reverse enteric coatings) or pH-independent.

The modified release coatings that may be employed include, but are not limited to, water-insoluble release modifiers or water-soluble release modifiers or combinations thereof. The water-insoluble release modifiers that may be employed include polymeric water-insoluble release modifier or non-polymeric water-insoluble release modifier or combinations thereof. Suitable polymeric water-insoluble release modifiers include, but are not limited to, cellulose polymers and derivatives thereof, polyacrylic acid and polymethacrylic acid polymers and derivatives thereof, maleic acid copolymers and derivatives thereof, polyvinyl derivatives; and the like or any combinations thereof. In one embodiment, suitable polymeric water-insoluble release modifiers include, but are not limited to, polyvinyl acetate, polyvinyl chloride, polyvinyl carbonate, ethyl cellulose, nitrocellulose, vinylidene chloride-acrylonitrile copolymer, acrylonitrile-styrene copolymer, ethylene vinyl acetate, cellulose acetate, cellulose acetate phthalate, cellulose acetate butyrate, copolymers of vinyl pyrrolidone, blend of polymers comprising polyvinyl acetate, hydroxypropyl methylcellulose phthalate, methacrylic acid copolymers such as Eudragit® L100/S100/L100-55 and the like or mixtures thereof; methacrylate copolymers such as Eudragit® E100/EPO, Eudragit® RL100/RL30D/RLPO, Eudragit® RS100/RS30D/RSPO and the like or mixtures thereof. Suitable non-polymeric water-insoluble release modifiers include, but are not limited to, fats, oils, waxes, fatty acids, fatty acid esters, glycerides, long chain monohydric alcohols and their esters, phospholipids, terpenes or combinations thereof. Suitable release modifiers in each of these categories have been listed hereinbefore.

In one embodiment, the coating is a pH-independent, water insoluble, water-permeable barrier coating which optionally contains one or more plasticizers, and which is optionally cured. Optionally, the coating includes a plasticizer is used in the percent range, or a mixture of plasticizers combine to total, about 2% w/w to about 50 w/w of the coating layer, or about 2.5% w/w to about 20% w/w of the coating layer on the coated drug-ion exchange resin complex. In certain embodiments, a plasticizer in range of about 5% w/w to about 10% w/w of the coating layer based on the coated complex provides the most desirable properties. Suitable plasticizers are water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor P, and mixtures thereof. Other plasticizers are described in Patent Application Publication No. US 2003/0099711 A1, May 29, 2003, page 4 (0041) the disclosure of which is incorporated herein by reference. In general, the plasticizer is selected to enhance high flexibility or elongation (elasticity) of the film coating at break measured by the texture analyzer TA-XT2 HiR (Stable Microsystems) and by the method reported by the manufacturer in its literature [i.e., Jan-Peter Mittwollen, Evaluation of the Mechanical Behavior of Different Sustained Release Polymers, Business Briefing: Pharmagenerics, 2003, pp. 1-3, BASF], of at least about 100% to about 400% or higher, of at least about 125% and preferably in a range between about 150% to about 400% while not substantially increasing the tackiness of the polymer film greater than about 2 (wherein the film is measured by the Hossel method referenced above independent of any composition on which it has been deposited).

In certain embodiments, the pH-independent barrier coating system contains polyvinyl acetate polymer, which in certain embodiments in applied as an aqueous coating dispersion. The polyvinylacetate is insoluble in water at room temperature and may be used in either substantially pure form or as a blend. A commercial blend contains primarily a polyvinyl acetate polymer, a stabilizer, and minor amounts of a surfactant such as sodium lauryl sulfate. More specifically, a desirable aqueous based coating solution is KOLLICOAT® SR 30 D (BASF Corporation) and whose composition is about 27% polyvinyl acetate, about 2.7% polyvinylpyrrolidone (PVP), about 0.3% sodium lauryl sulfate (solids content 30% w/w). In one embodiment, if a substantially pure form of PVA is used, it can be dissolved in a suitable non-aqueous solvent to provide a coating solution for the drug ion-exchange resin complex. The KOLLICOAT® SR-30D aqueous dispersion may be cured for about 1 to about 24 hours. In alternate embodiments, the coating is cured for about 4 to about 16 hours, and preferably about 5 hours at high temperature, e.g., about 50° C. to about 65° C., and preferably about 60° C. Where the barrier coating comprises polyvinyl acetate, the polyvinyl acetate is present in an amount of about 70% w/w to about 90% w/w of the final barrier coating layer, at least about 75% w/w, at least about 80% w/w, about 85% w/w of the final barrier coating layer. Where the barrier coating also comprises PVP as a stabilizer component (e.g., as is present in KOLLICOAT® SR 30D), the final barrier coating layer generally contains about 5 to about 10% w/w of polyvinyl pyrrolidone.

The non-polymeric water-insoluble release modifiers that may be employed in the compositions of the present invention include, but are not limited to, Cutina® (hydrogenated castor oil), Hydrobase® (hydrogenated soybean oil), Castorwax® (hydrogenated castor oil), Croduret® (hydrogenated castor oil), Carbowax®, Compritol® (glyceryl behenate), Sterotex® (hydrogenated cottonseed oil), Lubritab® (hydrogenated cottonseed oil), Apifil® (wax yellow), Akofine® (hydrogenated cottonseed oil), Softisan® (hydrogenated palm oil), Hydrocote® (hydrogenated soybean oil), Corona® (Lanolin), Gelucire® (macrogolglycerides Lauriques), Precirol® (glyceryl palmitostearate), Emulcire™ (cetyl alcohol), Plurol® diisostearique (polyglyceryl diisostearate), Geleol® (glyceryl stearate), and mixtures thereof. In another embodiment, lipids or waxes can also be employed in the form of an aqueous dispersion stabilized by surfactants and suitable stabilizers. Suitable water-soluble release modifiers that may be employed include, but are not limited to, cellulose polymers and derivatives thereof, gums, polyvinyl derivatives and the like or combinations thereof. In one embodiment, suitable water soluble release modifiers that may be employed include, but are not limited to, polyvinylpyrrolidone, poloxamer, guar gum, xanthan gum, fenugreek gum or galactomannan, gum arabic, fenugreek fibers comprising soluble and insoluble fibers, tragacanth, cellulose derivatives such as hydroxypropyl methylcellulose, hydroxypropyl cellulose, methylcellulose, and hydroxyethyl cellulose, carboxymethylethyl cellulose, hydroxyethylmethyl carboxymethyl cellulose, hydroxyethyl methyl cellulose, carboxymethyl cellulose, methylhydroxyethyl cellulose, methylhydroxypropyl cellulose or any mixtures thereof. In one embodiment the release modifier employed is ethyl cellulose. The release modifiers of the present invention may be used in admixture with at least one pharmaceutically acceptable excipient, such as but not limited to, plasticizers, pigments, anti-tacking agents and the like or any mixtures thereof. Suitable plasticizers include, but are not limited to, dibutyl sebacate, propylene glycol, polyethylene glycol, polyvinyl alcohol, triethyl citrate, acetyl triethyl citrate, acetyl tributyl citrate, tributyl citrate, triacetin or the like or any combinations thereof. Suitable anti-tacking agents that may be employed include, but are not limited to, talc, colloidal silicon dioxide and the like or combinations thereof. In a further embodiment, stabilizers as described under drug-resin complexes may be employed in the release rate modifier layer.

Any suitable coating procedure known to a person skilled in the art, which provides a substantially complete coating without significant agglomeration of the drug-ion exchange resin complex particles, may be used. Coating may be applied to the drug-resin complex particles by processes such as, but not limited to, melt coating, spray coating, pan coating, fluidized bed coating and the like. Coatings may be applied in a coating pan or with a fluid-bed coating apparatus. The release modifier coatings may be applied from aqueous suspension or organic solvents such as, but not limited to, isopropyl alcohol. Optionally after coating the coated drug-resin complexes may be cured at a suitable temperature and for a suitable amount of time. The term "substantially coated" as used herein means that the drug-ion exchange resin complex particles discussed herein above is substantially completely coated with the release modifier. While complete coating over the drug-resin complex particles, with release modifier is ideal, minor variations in this are possible in practice during coating and are therefore referred to as "substantially coated". Optimum coat weight and coat thickness may be determined and generally depends on the drug release characteristics of the resin for that particular active moiety. In one embodiment, the particles may be coated with at least one release modifier to a weight gain of about 1% to about 75%, or about 5% to about 60%, or about 10% to about 50%, or about 15% to about 40%, or about 5% to about 30%, or about 10% to about 25%, or values in between. In one embodiment the particles are variably coated at different levels of release modifier coating and the variably coated particles are present in particular proportions in the modified release compositions. The presence of such variably coated beads helps achieve the desired release profiles that does not result either in dose dumping or excessive release retardation. In one embodiment the compositions of the present invention comprise at least two variably coated populations of coated particles. In another embodiment at least two populations of variably coated particles are present in a ratio from about 1:99 to about 99:1. In one embodiment, coated and uncoated modified release particles may be incorporated in the compositions. The modified release particles may be present in the compositions in an amount from about 5% w/w to about 95 w/w of the GHB drug(s) and any optional additional biologically active moiety in the composition.

In certain embodiments, a barrier coating is present in amount of about 2% w/w to about 200% w/w of an uncoated drug, uncoated drug-ion exchange resin complex, or a precoated drug-ion exchange resin complex, i.e. a drug-ion exchange resin complex-matrix. In certain embodiments, the modified release barrier coating is a pH-independent, water-permeable, water-insoluble coating which is present in an amount of about 2% w/w to about 40% w/w, about 2% to about 35% w/w, about 2% w/w to about 30% w/w, about 5% w/w to 50% w/w, about 10% w/w to about 40% w/w, about 15% w/w, about 5% w/w, about 10% w/w, or about 15% w/w. In certain embodiments, the barrier coating is a blend comprising about 70% w/w to about 90% w/w polyvinylacetate, with at least one stabilizer and a plasticizer. In certain embodiments, the stabilizer is a polyvinylpyrrolidone and/or sodium lauryl sulfate.

In certain embodiments, a biologically active moiety (e.g., a drug), is included in a composition of the invention in combination with the GHB drug(s) in the form of a particle or granule which is not an ion exchange resin complex. In other embodiments, a biologically active moiety may be layered onto an ion exchange resin bead, or an inert (sugar) sphere bead to form a pellet or particle. Additionally, or alternatively, a "free" API or other "free" moiety may be admixed with other components and optionally coated, to form a granule, particle, or pellet, etc. In order to form a granule or particle, the GHB drug (or additional any active moiety/moieties used in the composition in combination with the GHB drug(s)) are typically admixed with suitable excipients. In certain embodiments, particles or granules are formed by admixing the drug(s) with one or more excipients to form a particle or granule which may optionally be coated with one or more of the coating materials described in the preceding paragraphs. Suitable excipients for inclusion in such particles or granules include, e.g., at least one release retarding agent, a binder, and/or a diluent, such as are described in the following paragraphs. Formation and coating of such particles and granules are known to those of skill in the art.

In certain embodiments, a drug-ion exchange resin complex (which may contain one or more different drugs) has been granulated with a hydrophilic or hydrophobic matrix forming polymer. In certain embodiments, the matrix forming polymer is present in an amount of about 5% w/w to about 40% w/w, or about 5% w/w to about 35% w/w, or about 5% w/w to about 30% w/w, or about 5% w/w to about 25% w/w, or about 5% w/w to about 20% w/w, or about 10% w/w to about 35% w/w, or about 15% w/w to about 35% w/w. based on the uncoated drug-ion exchange resin complex. In one embodiment, the matrix comprises a hydrophilic polymer, or a blend containing same, such as Kollidon® SR (80% polyvinyl acetate, 19% polyvinylpyrrolidone, 0.8% sodium lauryl sulfate, 0.2% Silica), available from BASF. Other hydrophilic polymers may be selected.

Pharmaceutically Acceptable Excipients

The compositions of the invention may be in liquid form, such a suspension, or in solid form (e.g., a powder, powder for suspension (POS), tablet, capsule, other suitable form). The excipients for the composition are selected accordingly. For example, excipients in a tablet may include binders, diluents, disintegrating agent, osmogents, release retarding polymers, flow aids, compression aids, lubricants and/or anti-adherents. Excipients in a capsule may include binders, diluents, release retarding polymers, flow aids. Excipients in a suspension, powder, pudding, paste and/or ER POS may include suspending agents and/or thickening agent, wetting agents, and/or preservatives. Excipients are discussed in subsequent section.

Tablet Excipients

Excipients in a tablet may include one or more of each: binders, diluents, superdisintegrant, osmogents, release retarding agent, flow aids, compression aids, lubricants and/or anti-adherents. One or more superdisintegrants can be selected from low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinised starch and sodium carboxymethyl starch. Examples of suitable binders include, but are not limited to, starch, pregelatinized starch, polyvinyl pyrrolidone (PVP), copovidone, cellulose derivatives, such as hydroxypropylmethyl cellulose (HPMC), hydroxypropyl cellulose (HPC) and carboxymethyl cellulose (CMC) and their salts. Examples of suitable diluents include, but are not limited to, starch, dicalcium phosphate, microcrystalline cellulose, lactose monohydrate, dextrate hydrated and the like. Examples of suitable lubricants include, but are not limited to, magnesium stearate, calcium stearate, stearic acid, talc, and sodium stearyl fumarate. Compositions may optionally also include a glidant such as, but not limited to, colloidal silica, silica gel, precipitated silica, or combinations thereof. Release retarding agent can be polymeric, or non-polymeric type. Release retardant can be pH dependent or pH independent. Release retardant may be hydrophilic or hydrophobic or both. hydrophobic release controlling agents are selected from the group comprising ammonio methacrylate copolymers type A and B as described in USP, methacrylic acid copolymer type A, B and C as described in USP, polyacrylate dispersion 30% as described in Ph. Eur., polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly (butyl methacrylate), polyisobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl acetylate), poly (octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate; glycerol monooleate, acetylated monoglycerides, tristearin, tripalmitin, cetyl esters wax, glyceryl palmitostearate, glyceryl behenate and hydrogenated castor oil. Examples of hydrophilic polymers suitable for use in this invention are cellulose polymers and their derivatives (such as for example, hydroxyethylcellulose, hydroxypropylcellulose, hypromellose, carboxymethylcellulose, polysaccharides and their derivatives, polyalkylene oxides, polyethylene glycols, chitosan, poly(vinyl alcohol), xanthan gum, maleic anhydride copolymers, starch-based polymers, crosslinked polyacrylic acids and their derivatives, e.g., a carbomer homopolymer, Kollidon® SR (PVA PVP copolymer). Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide; xanthan gum; hydroxypropylmethyl cellulose; or mixtures thereof.

In certain embodiments, a modified release tablet comprises i. at least a GHB drug(s) optionally granulated and/or coated with release retardant ii. an IPN forming blend optionally comprising a (semi or full) IPN, comprising at least one anionic polymer, at least one galactomannan, and at least two cross linking agents iii. At least one gas generating agent iv. at least one super-disintegrant v. at least one binder vi. lubricant and flow aid. In certain embodiments, a modified release tablet comprises i. at least a GHB drug(s) granulated with matrix forming release retardant forming release retardant (e.g., polyvinylacetate and coated with water permeable diffusion barrier forming release retardant (5% w/w, 2-20% w/w) Kollicoat® SR 30D. ii. an IPN forming blend, optionally comprising a (semi or full) IPN, comprising pectin (10% w/w, 5-30% w/w), guar gum (10% w/w, 5-30% w/w), borax (2% w/w, 1-6% w/w) and calcium chloride (5% w/w, 2-15% w/w). iii. Gas generating agent, Calcium carbonate (5% w/w, 2-15% w/w) iv. Superdisintegrating agent Crospovidone (13% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w). In certain embodiments, a composition comprises i. at least one GHB drug(s) optionally granulated and/or coated with release retardant ii. an IPN forming blend, optionally comprising a (semi or full) IPN, comprising at least two anionic polymers and at least one cross linking agent iii. At least one gas generating agent iv. at least one super-disintegrant v. at least one binder vi. a lubricant and flow aid. In certain embodiments, a composition (e.g. a modified release tablet), comprises i. at least one GHB drug(s) granulated with a pH-independent matrix forming release retardant (e.g., polyvinylacetate, or a blend containing same, such as Kollidon® SR (80% PVAc, 19% Povidone, 0.8% SLS, 0.2% Silica), available from BASF (15% w/w, 5-40% w/w) and coated with water permeable pH-independent diffusion barrier forming release retardant (15% w/w, 2-20% w/w)(e.g., a polyvinylacetate blend such as Kollicoat® SR 30D (polyvinyl acetate stabilized with polyvinylpyrrolidone and sodium lauryl sulfate)). ii. an IPN forming blend, optionally comprising a (semi or full) IPN comprising pectin (10% w/w, 5-30% w/w) (anionic polymer), carrageenan iota (10% w/w, 5-30% w/w) (anionic polymer), and calcium chloride (5% w/w, 2-15% w/w). iii. Gas generating agent, Calcium carbonate (5% w/w, 2-15% w/w) iv. Superdisintegrating agent Crospovidone (18% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) optionally granulated and/or coated with release retardant ii. an IPN forming blend, optionally comprising a (semi or full) IPN, comprising at least one galactomannan, at least one anionic polymer, at least one non-ionic polymer and at least two cross linking agents iii. At least one gas generating agent iv. at least one super-disintegrant v. at least one binder vi. a lubricant and flow aid. In certain embodiments, a modified release tablet comprises i. at least one GHB drug(s) granulated with of a pH-independent matrix forming release retardant (e.g., polyvinylacetate, or a blend containing same, such as Kollidon® SR (80% PVAc, 19% Povidone, 0.8% SLS, 0.2% Silica), available from BASF (2% w/w, 1-40% w/w) and coated with a water permeable pH-independent diffusion barrier forming release retardant (e.g., a polyvinylacetate blend such as Kollicoat® SR 30D (polyvinyl acetate stabilized with polyvinylpyrrolidone and sodium lauryl sulfate))(1% w/w, 0.5-20% w/w). ii. an IPN forming blend, optionally comprising a (semi or full) IPN, comprising pectin (10% w/w, 5-30% w/w), fenugreek gum (10% w/w, 5-20% w/w), HPMC K100M (3% w/w, 1-20% w/w), calcium chloride (7% w/w, 2-15% w/w) and borax (5% w/w, 2.5-10% w/w). iii. Gas generating agent, Calcium carbonate (15% w/w, 5-15% w/w) iv. Superdisintegrating agent Crospovidone (25% w/w, 6-40% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) optionally granulated and/or coated with release retardant ii. an IPN forming blend, optionally comprising a (semi or full) IPN, comprising at least one galactomannan, at least two anionic polymers, at least one non-ionic polymer and at least two cross linking agents iii. At least one gas generating agent iv. at least one super-disintegrant v. at least one binder vi. a lubricant and flow aid. In certain embodiments, a modified release tablet comprises i. at least one GHB drug(s) granulated with matrix forming release retardant (e.g., Kollidon® SR) (2% w/w, 1-40% w/w) and coated with water permeable diffusion barrier forming release retardant or about 1% w/w) (e.g., Kollicoat SR 30D). ii. an IPN forming blend, optionally comprising a (semi or full) IPN, comprising pectin (5% w/w, 3-15% w/w), carrageenan iota (5% w/w, 3-15% w/w), fenugreek gum (10% w/w, 5-20% w/w), HPMC K100M (3% w/w, 1-20% w/w), calcium chloride (7% w/w, 2-15% w/w) and borax (5% w/w, 2.5-10% w/w). Gas generating agent, Calcium carbonate (15% w/w, 5-15% w/w) iv. Superdisintegrating agent Crospovidone (25% w/w, 6-40% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) optionally granulated and/or coated with release retardant ii. an IPN forming blend, optionally comprising a (semi or full) IPN, comprising at least two galactomannan polymers and at least one cross linking agent iii. At least one gas generating agent iv. at least one super-disintegrant v. at least one binder vi. a lubricant and flow aid. In certain embodiments, a modified release tablet comprises i. at least one GHB drug(s) granulated with matrix forming release retardant (e.g., Kollidon® SR) (10% w/w, 5-40% w/w) and coated with water permeable diffusion barrier forming release retardant (5% w/w, 2-20% w/w) (e.g., Kollicoat® SR 30D). ii. an IPN forming blend, optionally comprising a (semi or full) IPN, comprising fenugreek gum (10% w/w, 5-30% w/w), guar gum (10% w/w, 5-30% w/w), borax (8% w/w, 4-24% w/w). iii. Gas generating agent, Calcium carbonate (5% w/w, 2-15% w/w) iv. Superdisintegrating agent Crospovidone (13% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) optionally granulated and/or coated with release retardant ii. an IPN forming blend, optionally comprising a (semi or full) IPN, comprising at least two galactomannan polymers, at least one anionic polymer and at least two cross linking agents iii. At least one gas generating agent iv. at least one super-disintegrant v. at least one binder vi. a lubricant and flow aid. In certain embodiments, a modified release tablet comprises i. at least one GHB drug(s) granulated with matrix forming release retardant (e.g., Kollidon® SR) (10% w/w, 5-40% w/w) and coated with water permeable diffusion barrier forming release retardant (5% w/w, 2-20% w/w) (e.g., Kollicoat® SR 30D). ii. an IPN forming blend, optionally comprising a (semi or full) IPN, comprising Pectin (anionic polymer) (10% w/w, 5-30% w/w), fenugreek gum (galactomannan) (5% w/w, 3-15% w/w), guar gum (galactomannan) (5% w/w, 3-15% w/w), borax (4% w/w, 2-12% w/w) (crosslinking agent) and calcium chloride (crosslinking agent) (5% w/w, 2-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) optionally granulated and/or coated with release retardant ii. an IPN forming blend, optionally comprising a (semi or full) IPN, comprising at least two galactomannan polymers, at least one anionic polymer, at least one non-ionic polymer and at least two cross linking agents iii. At least one gas generating agent iv. at least one super-disintegrant v. at least one binder vi. a lubricant and flow aid. In certain embodiments, a modified release tablet comprises i. at least one GHB drug(s) granulated with matrix forming release retardant (e.g., Kollidon® SR) (10% w/w, 5-40% w/w) and coated with water permeable diffusion barrier forming release retardant (5% w/w, 2-20% w/w) (e.g., Kollicoat® SR 30D). ii. an IPN forming blend, optionally comprising a (semi or full) IPN, comprising Pectin (anionic polymer) (10% w/w, 5-30% w/w), fenugreek gum (5% w/w, 3-15% w/w) (galactomannan), guar gum (5% w/w, 3-15% w/w) (galactomannan), HPMC K100M (5% w/w, 2-15% w/w) (non-ionic polymer), borax (4% w/w, 2-12% w/w) (crosslinking agent) and calcium chloride (5% w/w, 2-15% w/w) (crosslinking agent). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) optionally granulated and/or coated with release retardant ii. an IPN forming blend, optionally comprising a (semi or full) IPN, comprising at least two galactomannan polymers, at least one non-ionic polymer and at one cross linking agent iii. At least one gas generating agent iv. at least one super-disintegrant v. at least one binder vi. a lubricant and flow aid. In certain embodiments, a modified release tablet comprises i. at least one GHB drug(s) granulated with matrix forming release retardant (e.g., Kollidon® SR) (10% w/w, 5-40% w/w) and coated with water permeable diffusion barrier forming release retardant (5% w/w, 2-20% w/w) (e.g., Kollicoat® SR 30D). ii. an IPN forming blend, optionally comprising a (semi or full) IPN, comprising Pectin (10% w/w, 5-30% w/w), fenugreek gum (10% w/w, 3-25% w/w), guar gum (5% w/w, 3-15% w/w), HPMC K100M (5% w/w, 2-15% w/w), borax (6% w/w, 2-15% w/w) iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming blend, optionally comprising a (semi or full) IPN, comprising at least one anionic polymer, at least one galactomannan, and at least two cross linking agents iii. At least one gas generating agent iv. at least one super-disintegrant v. at least one binder vi. lubricant and flow aid. In certain embodiments, a modified release tablet comprises. i. drug-ion exchange resin complex granulated with matrix forming release retardant (e.g., Kollidon® SR) (10% w/w, 5-40% w/w) and coated with water permeable diffusion barrier forming release retardant (5% w/w, 2-20% w/w) (e.g., Kollicoat® SR 30D). ii. an IPN forming blend, optionally comprising a (semi or full) IPN, comprising Pectin (10% w/w, 5-30% w/w), fenugreek gum (5% w/w, 3-15% w/w), borax (4% w/w, 2-12% w/w) and calcium chloride (5% w/w, 2-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming blend, optionally comprising a (semi or full) IPN, comprising at least two anionic polymers and at least one cross linking agent iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (10% w/w, 5-40% w/w) and coated with water permeable diffusion barrier forming release retardant (5% w/w, 2-20% w/w) Kollicoat® SR 30D. ii. an IPN forming blend, optionally comprising a (semi or full) IPN, comprising Pectin (10% w/w, 5-30% w/w), Carrageenan iota (5% w/w, 3-15% w/w), and calcium chloride (5% w/w, 2-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming blend, optionally comprising a (semi or full) IPN, comprising at least one galactomannan, at least one anionic polymer, at least one non-ionic polymer and at least two cross linking agents iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (10% w/w, 5-40% w/w) and coated with water permeable diffusion barrier forming release retardant (5% w/w, 2-20% w/w) Kollicoat® SR 30D. ii. an IPN forming blend, optionally comprising a (semi or full) IPN, comprising Pectin (10% w/w, 5-30% w/w), Guar gum (5% w/w, 3-15% w/w), HPMC K100M (5% w/w, 2-20% w/w), Borax (2% w/w, 0.8-6% w/w) and calcium chloride (5% w/w, 2-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming blend, optionally comprising a (semi or full) IPN comprising at least one galactomannan, at least two anionic polymers, at least one non-ionic polymer and at least two cross linking agents iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (5% w/w, 2-20% w/w) and coated with water permeable diffusion barrier forming release retardant (2% w/w, 0.5-15% w/w) Kollicoat® SR 30D. ii. an IPN forming blend, optionally comprising a (semi or full) IPN, comprising Guar gum (5% w/w, 2-15% w/w), Pectin (5% w/w, 5-30% w/w), Carrageenan iota (5% w/w, 3-15% w/w), HPMC K100M (5% w/w, 2-20% w/w), Borax (1% w/w, 0.4-3% w/w) and calcium chloride (5% w/w, 2-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming system, optionally comprising a (semi or full) IPN, comprising at least two galactomannan polymers and at least one cross linking agent iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (5% w/w, 2-20% w/w) and coated with water permeable diffusion barrier forming release retardant (2% w/w, 0.5-15% w/w) Kollicoat® SR 30D. ii. an IPN forming blend, optionally comprising a (semi or full) IPN, comprising Guar gum (10% w/w, 2-20% w/w), Fenugreek gum (10% w/w, 5-30% w/w), and Borax (8% w/w, 3-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. at least one GHB drug(s) (e.g., API or any salt thereof) optionally granulated and/or coated with release retardant ii. an IPN forming blend, optionally comprising a (semi or full) IPN, comprising at least two galactomannan polymers, at least one anionic polymer and at least two cross linking agents iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (5% w/w, 2-20% w/w) and coated with water permeable diffusion barrier forming release retardant (2% w/w, 0.5-15% w/w) Kollicoat® SR 30D. ii. an IPN forming blend, optionally comprising a (semi or full) IPN, comprising Guar gum (5% w/w, 2-20% w/w), Fenugreek gum (5% w/w, 5-30% w/w), Carrageenan kappa (5% w/w, 2-20% w/w), potassium citrate (1% w/w, 0.5-5% w/w) and Borax (8% w/w, 3-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming blend, optionally comprising a (semi or full) IPN, comprising at least two galactomannan polymers, at least one anionic polymer, at least one non-ionic polymer and at least two cross linking agents iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (5% w/w, 2-20% w/w) and coated with water permeable diffusion barrier forming release retardant (2% w/w, 0.5-15% w/w) Kollicoat® SR 30D. ii. an IPN forming blend, optionally comprising a (semi or full) IPN, comprising Guar gum (5% w/w, 2-20% w/w), Fenugreek gum (5% w/w, 5-30% w/w), Carrageenan kappa (5% w/w, 2-20% w/w), HPMC K100M (5% w/w, 1-15% w/w), potassium citrate (1% w/w, 0.5-5% w/w) and Borax (8% w/w, 3-15% w/w). iii. Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises i. drug-ion exchange resin complex optionally granulated and/or coated with release retardant ii. an IPN forming blend, optionally comprising a (semi or full) IPN, comprising at least two galactomannan polymers, at least one non-ionic polymer and at one cross linking agent iii. At least one gas generating agent iv. at least one super-disintegrant v. at least one binder vi. a lubricant and flow aid. In certain embodiments, a modified release tablet comprises. i. drug-ion exchange resin complex granulated with matrix forming release retardant Kollidon® SR (5% w/w, 2-20% w/w) and coated with water permeable diffusion barrier forming release retardant (2% w/w, 0.5-15% w/w) Kollicoat® SR 30D. ii. an IPN forming blend, optionally comprising a (semi or full) IPN, comprising Guar gum (5% w/w, 2-20% w/w), Fenugreek gum (5% w/w, 5-30% w/w), HPMC K100M (5% w/w, 2-20% w/w), and Borax (8% w/w, 3-15% w/w). Gas generating agent, Calcium carbonate (5% w/w, 2-15% w/w) iv. Superdisintegrating agent Crospovidone (10% w/w, 6-25% w/w) v. Binder copovidone (5% w/w, 3-10% w/w) vi. Magnesium stearate (0.5% w/w, 0.5-2% w/w) and colloidal silicon dioxide (0.02% w/w, 0.1-1% w/w).

In certain embodiments, a modified release tablet comprises components as per any of the above embodiments plus one or more liquid crystal forming substances.

In certain embodiments, a modified release tablet comprises components as per any of the above embodiments plus one or more liquid crystal forming substances.

Suspension Excipients

In certain embodiments, a powder composition comprising a floating IPN system is reconstituted with an aqueous media to form a pudding (or paste) or suspension. In certain embodiments, the sole ingredient used for this reconstitution is water (e.g., a purified water, deionized water, or tap or bottled water). In other embodiments, the water is included in an aqueous suspension base which may include various excipients in addition to water. Optionally, the suspension base may include one or more additional components of the IPN forming system and/or an additional active ingredient. Preferably, for reconstitution, the amount of the floating IPN system to water ratio is controlled. In certain embodiments, the) powder composition to water ratio is about 1 to about 0.1 to about 1 to about 15 (1:0.1 to 1:15). In certain embodiments, the powder to water ratio is about 1 to about 0.5 to about 1 to about 10 (1:0.5 to 1:10). In other embodiments, the powder to water ratio is about 1 to about 2 to about 1 to about 7 (1:2 to 1:7). In certain embodiments, the product reconstituted according to these powder: water ratios is a suspension (e.g., at a solid content of less than 20 wt %), a pudding or a paste (e.g., at a solids content of 20 wt % to 50 wt %).

An aqueous suspension base may further include one or more additional excipients. Such excipients may include, e.g., one or more of each of the following: binders, diluents, salivating agents, surfactants, flavors, sweeteners, colorants, souring agents, viscolizers, glidants, chelating agents, lubricants, solubilizers, stabilizers, suspending agents, preservatives, cosolvents, anti-caking agents, buffers and/or the like or any combinations thereof. Examples of suitable binders include, but are not limited to, starch, pregelatinized starch, polyvinyl pyrrolidone, copovidone, cellulose derivatives, such as hydroxypropylmethyl cellulose, hydroxypropyl cellulose and carboxymethyl cellulose and their salts. Examples of suitable diluents include, but are not limited to, starch, microcrystalline cellulose, lactose, xylitol, mannitol, maltose, polyols, fructose, guar gum, sorbitol, magnesium hydroxide, dicalcium phosphate, coprocessed mannitol and calcium silicate and the like or any combinations thereof. Examples of lubricants include, but are not limited to, magnesium stearate, calcium stearate, stearic acid, talc, and sodium stearyl fumarate. Suitable glidants includes but are not limited to, colloidal silica, silica gel, precipitated silica, or combinations thereof. Suitable salivating agents include, but are not limited to, micronized polyethylene glycol, sodium chloride or precipitated micronized silica. Examples of solubilizers include, but are not limited to cetostearyl alcohol, cholesterol, diethanolamine, ethyl oleate, ethylene glycol palmitostearate, glycerin, glyceryl monostearate, isopropyl myristate, lecithin, medium-chain glyceride, monoethanolamine, oleic acid, propylene glycol, polyoxyethylene alkyl ether, polyoxyethylene castor oil glycoside, polyoxyethylene sorbitan fatty acid ester, polyethylene sorbitan fatty acid ester, polyoxyethylene stearate, propylene glycol alginate, sorbitan fatty acid ester, stearic acid, sunflower oil, triethanolamine, or combinations thereof. Souring agents include, but are not limited to, monosodium fumarate and/or citric acid. The compositions of the present invention may also include stabilizers such as, but not limited to, those described above under drug-resin complexes. Suitable chelating agents that may be employed have been discussed herein above. Suitable viscolizers include, but are not limited to, coprocessed microcrystalline cellulose such as but not limited to, Avicel RC591, Avicel CL-611, D-sorbitol solution, polyalkylene oxides such as, but not limited to polyethylene oxide; cellulose ethers such as, but not limited to hydroxyethyl cellulose, hydroxypropylcellulose, hydroxypropyl methyl cellulose, methyl cellulose, ethyl cellulose, sodium carboxy methylcellulose, calcium carboxymethyl cellulose, microcrystalline cellulose; gums such as but not limited to gum arabic alginates, agar, sodium alginate guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan; polyols such as, but not limited to dipropylene glycol, polypropylene glycol, propylene glycol, polyethylene glycol (PEG), sorbitol and glycerol; carbopol, starch and starch-based polymers such as, but not limited to, pregelatinized starch, acrylic acid and methacrylic acid polymers, and esters thereof, maleic anhydride polymers; polymaleic acid; poly(acrylamides); poly(olefinic alcohol)s; poly(N-vinyl lactams); polyoxyethylated saccharides; polyoxazolines; polyvinylamines; polyvinylacetates; polyimines; povidone, vinylpyrrolidone/vinyl acetate copolymer and polyvinyl acetate, mixture of polyvinyl acetate and polyvinylpyrrolidone, chitin, cyclodextrin, gelatin, chitosan and the like or any mixtures thereof. Suitable surfactants include, but are not limited to, anionic, nonionic, cationic, and zwitterionic surfactants or a mixture thereof. The non-ionic surfactants employed in the composition may include, but are not limited to, ethoxylated fatty acid ester, ethoxylated fatty acid ethers, ethoxylated sorbitan ethers, ethoxylated alkyl-phenols, glycerol esters, glycerol sugar esters, polyoxyethyleneglycerol monolaurate, polyoxyethyleneglycerol monostearate, polyoxyethylene-20-cetyl stearate, polyoxyethylene-25-cetyl stearate, polyoxyethylene (25)-oxypropylene monostearate, polyoxyethylene-20-sorbitan monopalmitate, poly-oxyethylene-16-tert-octyl phenol, polyoxyethylene-20-cetyl ether, polyethylene glycol (1000) monocetyl ether, ethoxylated castor oil, polyoxyethylene sorbitol-lanolin derivatives, polyoxyethylene(25)propylene glycol stearate, polyoxyethylenesorbitol esters, polyoxyethylene-20-sorbitan monopalmitate, polyoxyethylene-16-tert-octylphenol, polyoxyethylene-20-cetyl ether, glycyeryl undecylenate and Polysorbate 60, capmul (medium chain glyceride), peceol (glyceryl monooleate), glyceryl laurate and glyceryl caprylate (Capmul MCM), PEG sorbitan fatty acid esters like PEG-20 sorbitan monolaurate (Tween 20), PEG-20 sorbitan monostearate (Tween 60), PEG-20 sorbitan monooleate (Tween 80), sorbitan fatty acid esters like sorbitan monolaurate (Span 20), glyceryl stearate (Cithrol GMS) or the like and mixtures thereof. Suitable cationic surfactants include, but are not limited to, quaternary ammonium compounds, alkylamidoamines and quaternary ester compounds, distearyl dimethyl ammonium chloride, dimyristyl dimethyl ammonium chloride, dipalmityl dimethyl ammonium chloride or the like and mixtures thereof. Suitable anionic surfactants include, but are not limited to, fatty alcohol sulfates, alpha olefin sulfonates, sulfosuccinates, phosphate esters, carboxylates, sarcosinates, alkyl benzene sulfonates, alkyl sulfonates, olefin sulfonates, alkyl ethersulfonates, glycerol ethersulfonates, a-methyl estersulfonates, sulfonic fatty acids, alkyl sulfates, fatty alcohol ethersulfates, glycerol ethersulfates, mixed hydroxy ethersulfates, monoglyceride (ether)sulfates, fatty acid amide (ether)sulfates, sulfosuccinates, sulfosuccinamates, sulfotriglycerides, amide soaps, ether carboxylic acids, isethionates, sarcosinates, taurides, alkyl oligoglycoside sulfates, alkyl (ether)phosphates or the like and mixtures thereof. Suitable zwitterionic surfactants employed include, but are not limited to, N-alkyl-N,N-dimethyl ammonium glycinates, for example cocoalkyl dimethyl ammonium glycinate, N-acyl aminopropyl-N,N-dimethyl ammonium glycinates, cocoacyl aminoethyl hydroxyethyl carboxymethyl glycinate or the like and mixtures thereof. Further, the composition of the present invention may further comprise a preservative such as but not limited to methyl parahydroxybenzoate, propyl parahydroxybenzoate and sodium benzoate. Suitable cosolvent that may be used includes, but is not limited to, ethanol and polyhydric alcohols such as, but not limited to, glycerin, propylene glycol, low molecular weight polyethylene glycols, and mixtures thereof. Further anti-caking agents that may be optionally incorporated include, but are not limited to, colloidal silicon dioxide, tribasic calcium phosphate, powdered cellulose, magnesium trisilicate, starch, and mixtures thereof. Suitable sweetening agent includes, but is not limited to, aspartame, stevia extract, glycyrrhiza, saccharine, saccharine sodium, acesulfame, sucralose, dipotassium glycyrrhizinate, galactose, fructose, high fructose corn syrup, dextrose, sucrose, sugar, maltose, partially hydrolyzed starch, corn syrup solids, sorbitol, xylitol, mannitol and the like or mixtures thereof. The compositions may comprise one or more natural and/or artificial flavors such as, but not limited to, mint flavor, orange flavor, lemon flavors, strawberry aroma, vanilla flavor, raspberry aroma, cherry flavor, tutti fruity flavor, magnasweet 135, key lime flavor, grape flavor, and fruit extracts and the like. Suitable colorants include, but are not limited to, pigments and dyes such as FD&C Red, FD&C Yellow, FD&C Green, and FD&C Blue and the like or combinations thereof.

Illustrative powder compositions are provided below. As used herein, a "powder for suspension" or "POS" refers to a composition which is formulated as a powder which designed to be suspended in a suspension base (e.g., purified water) prior to oral ingestion by a patient. In certain embodiments, the total amount of water (or other aqueous solution) is in the ratio provided and incorporated by reference therein. In certain embodiments, the powder is reconstituted in the form of a pudding or paste.

The exemplary combinations of recited components from the section relating to modified release tablets herein is incorporated by reference into this section. The weight percentages from this section are hereby incorporated by reference as well, with the total weight being based on the powder, or the solids in the suspension, rather than the total tablet.

In certain embodiments, a modified release powder comprises i. drug-ion exchange resin complex ii. drug-ion exchange resin complex coated with water permeable diffusion barrier iii. an IPN forming blend, optionally comprising a (full or semi) IPN, comprising at least one anionic polymer, at least one galactomannan, and at least two cross linking agents and iv. At least one gas generating agent.

In certain embodiments, a modified release powder comprise i. drug-ion exchange resin complex ii. drug-ion exchange resin complex coated with water permeable diffusion barrier iii. an IPN forming blend, optionally comprising a (full or semi) IPN, comprising at least two anionic polymers and at least one cross linking agent and iv. At least one gas generating agent.

In certain embodiments, a modified release powder comprises i. drug-ion exchange resin complex ii. drug-ion exchange resin complex coated with water permeable diffusion barrier iii. an IPN forming blend, optionally comprising a (full or semi) IPN, comprising at least one galactomannan, at least one anionic polymer, at least one nonionic polymer and at least two cross linking agents and iv. At least one gas generating agent.

In certain embodiments, a modified release powder comprises i. drug-ion exchange resin complex ii. drug-ion exchange resin complex coated with water permeable diffusion barrier iii. a IPN forming blend, optionally comprising a (full or semi) IPN, comprising at least one galactomannan, at least two anionic polymers, at least one non-ionic polymer and at least two cross linking agents and iv. At least one gas generating agent.

In certain embodiments, a modified release powder comprises i. drug-ion exchange resin complex ii. drug-ion exchange resin complex coated with water permeable diffusion barrier iii. an IPN forming blend, optionally comprising a (full or semi) IPN, comprising at least two galactomannan polymers and at least one cross linking agent and iv. At least one gas generating agent.

In certain embodiments, a modified release powder comprises i. drug-ion exchange resin complex ii. drug-ion exchange resin complex coated with water permeable diffusion barrier iii. an IPN forming blend, optionally comprising a (full or semi) IPN, comprising at least two galactomannan polymers, at least one anionic polymer and at least two cross linking agents and iv. At least one gas generating agent.

In certain embodiments, a modified release powder comprises i. drug-ion exchange resin complex ii. drug-ion exchange resin complex coated with water permeable diffusion barrier iii. an IPN forming blend, optionally comprising a (full or semi) IPN, comprising at least two galactomannan polymers, at least one anionic polymer, at least one non-ionic polymer and at least two cross linking agents and iv. At least one gas generating agent.

In certain embodiments, a modified release powder comprises i. drug-ion exchange resin complex ii. drug-ion exchange resin complex coated with water permeable diffusion barrier iii. an IPN forming blend, optionally comprising a (full or semi) IPN, comprising at least two galactomannan polymers, at least one non-ionic polymer and at one cross linking agent and iv. At least one gas generating agent.

In certain embodiments, a modified release powder comprises i. Granules comprising a at least one GHB drug(s), a diluent and a binder ii. Granules comprising a at least one GHB drug(s), at least one release retarding agent, a binder and optionally a diluent that are coated with water permeable diffusion barrier iii. an IPN forming blend, optionally comprising a (full or semi) IPN, comprising at least one anionic polymer, at least one galactomannan, and at least two cross linking agents and iv. At least one gas generating agent In certain embodiments, a modified release powder comprises i. Granules comprising a at least one GHB drug(s), a diluent and a binder ii. Granules comprising a at least one GHB drug(s), at least one release retarding agent, a binder and optionally a diluent that are coated with water permeable diffusion barrier iii. a IPN forming blend, optionally comprising a (full or semi) IPN, comprising at least one anionic polymer, at least two galactomannans, at least one non-ionic polymer and at least two cross linking agents and iv. At least one gas generating agent.

In certain embodiments, a modified release powder comprises i. Granules comprising at least one GHB drug(s), a diluent and a binder ii. Granules comprising at least one GHB drug(s), at least one release retarding agent, a binder and optionally a diluent that are coated with water permeable diffusion barrier iii. an IPN forming blend, optionally comprising a (full or semi) IPN, comprising at least one anionic polymer, at least two galactomannans and at least two cross linking agents and iv. At least one gas generating agent.

In certain embodiments, a modified release powder comprises i. Granules comprising at least one GHB drug(s), a diluent and a binder ii. Granules comprising at least one GHB drug(s), at least one release retarding agent, a binder and optionally a diluent that are coated with water permeable diffusion barrier iii. an IPN forming blend, optionally comprising a (full or semi) IPN, comprising at least one anionic polymer, at least one galactomannan, at least one non-ionic polymer and at least two cross linking agents and iv. At least one gas generating agent.

In certain embodiments, a modified release powder comprises i. Granules comprising at least one GHB drug(s), a diluent and a binder ii. Granules comprising at least one GHB drug(s), at least one release retarding agent, a binder and optionally a diluent that are coated with water permeable diffusion barrier iii. an IPN forming blend, optionally comprising a (full or semi) IPN, comprising at least two galactomannans, at least one non-ionic polymer and at least one cross linking agent and iv. At least one gas generating agent.

In certain embodiments, a modified release powder comprises i. Granules comprising at least one GHB drug(s), a diluent and a binder ii. Granules comprising at least one GHB drug(s), at least one release retarding agent, a binder and optionally a diluent that are coated with water permeable diffusion barrier iii. an IPN forming blend, optionally comprising a (full or semi) IPN, comprising at least two anionic polymers, at least one galactomannan, and at least two cross linking agents and iv. At least one gas generating agent.

In certain embodiments, a modified release powder comprises i. Granules comprising at least one GHB drug(s), a diluent and a binder ii. Granules comprising at least one GHB drug(s), at least one release retarding agent, a binder and optionally a diluent that are coated with water permeable diffusion barrier iii. an IPN forming blend, optionally comprising a (full or semi) IPN, comprising at least two anionic polymers, at least one non-ionic polymer and at least one cross linking agent and iv. At least one gas generating agent.

In certain embodiments, a modified release powder comprises i. Granules comprising at least one GHB drug(s), a diluent and a binder ii. Granules comprising at least one GHB drug(s), at least one release retarding agent, a binder and optionally a diluent that are coated with water permeable diffusion barrier iii. drug-ion exchange resin complex iv. drug-ion exchange resin complex coated with water permeable diffusion barrier v. an IPN forming blend, optionally comprising a (full or semi) IPN, comprising at least one IPN forming anionic polymer, or at least one IPN forming galactomannan polysaccharide and at least one cross linking agent which interacts with at least one IPN forming anionic polymer or galactomannan to form an IPN and iv. At least one gas generating agent.

In certain embodiments, an orally administrable composition is provided which comprises at least one GHB drug and a floating IPN forming system comprising at least one non-toxic gas generating agent, two or more anionic polymers, and at least one cross-linking agent. In certain embodiments, the composition comprises two or more anionic polymers comprise 10 wt % to 40 wt % of the composition, based on the total dry components (e.g., powder blend). In certain embodiments, the anionic polymers are selected from pectin, gellan gum and/or carrageenan. In certain embodiments, the cross-linking agent(s) comprises about 5 wt % to 15 wt %, or 5 wt % to 12 wt %, or about 11 wt % or 6 wt % to 8 wt %, or about 7 wt % of the composition based on the total dry components (e.g., powder blend). In certain embodiments, the gas generating agent(s) comprises about 5 wt % to about 15 wt %, or 7 wt % to about 12 wt %, or about 7 wt %, or about 11 wt % of the composition based on the total dry components (e.g., powder blend). In certain embodiments, the gas generating agent is a bicarbonate. In certain embodiments, the bicarbonate is a potassium bicarbonate. In certain embodiments, the remainder of the composition comprises excipients such as diluents, binders, disintegrating agents, and the like.

In certain embodiments, the composition comprising the floating IPN forming system comprises components as per any of the above embodiments plus one or more liquid crystal forming substances.

In certain embodiments, the modified release powder is provided with components as per any of the embodiments along with suspension base which contains one or more IPN forming polymers in dissolved state and one or more cross-linking agents in dissolved and/or suspended state. Any of these modified release powders may be combined with a liquid to form a pudding, paste or suspension. Such puddings, pastes or powder-to-suspension (POS) may be reconstituted using said suspension base at the time of administration. The product forms a floating IPN in situ.

Although the following embodiments refer to suspension products, it will be understood that by controlling the amount of water or suspension base used as describe in this specification and incorporated herein, the product may be formulated as a suspension, pudding or paste. As described herein, water may be used rather than a suspension base, regardless of whether the product is to be delivered as a suspension, pudding or paste.

In certain embodiments, a modified release suspension comprises i. drug-ion exchange resin complex ii. drug-ion exchange resin complex coated with water permeable diffusion barrier iii. an IPN forming system, optionally comprising a (semi or full) IPN, comprising at least one anionic polymer, at least one galactomannan, and at least two cross linking agents iii. At least one gas generating agent and iv. A suspension base.

In certain embodiments, a modified release suspension comprises i. drug-ion exchange resin complex ii. drug-ion exchange resin complex coated with water permeable diffusion barrier iii. an IPN forming system, optionally comprising a (semi or full) IPN, comprising at least two anionic polymers and at least one cross linking agent iv. At least one gas generating agent and v. A suspension base.

In certain embodiments, a modified release suspension comprises i. drug-ion exchange resin complex ii. drug-ion exchange resin complex coated with water permeable diffusion barrier iii. an IPN forming system, optionally comprising a (semi or full) IPN, comprising at least one galactomannan, at least one anionic polymer, at least one non-ionic polymer and at least two cross linking agents iv. At least one gas generating agent and v. A suspension base.

In certain embodiments, a modified release suspension comprises i. drug-ion exchange resin complex ii. drug-ion exchange resin complex coated with water permeable diffusion barrier iii. an IPN forming system, optionally comprising a (semi or full) IPN, comprising at least one galactomannan, at least two anionic polymers, at least one non-ionic polymer and at least two cross linking agents iv. At least one gas generating agent and v. A suspension base.

In certain embodiments, a modified release suspension comprises i. drug-ion exchange resin complex ii. drug-ion exchange resin complex coated with water permeable diffusion barrier iii. an IPN forming system, optionally comprising a (semi or full) IPN, comprising at least two galactomannan polymers, at least one anionic polymer and at least two cross linking agents iv. At least one gas generating agent and v. A suspension base.

In certain embodiments, a modified release suspension comprises i. drug-ion exchange resin complex ii. drug-ion exchange resin complex coated with water permeable diffusion barrier iii. an IPN forming system, optionally comprising a (semi or full) IPN, comprising at least two galactomannan polymers, at least one anionic polymer, at least one non-ionic polymer and at least two cross linking agents iv. At least one gas generating agent and v. A suspension base.

In certain embodiments, a modified release suspension comprises components as per any of the above embodiments plus one or more liquid crystal forming substances.

In certain embodiments, the modified release products provided herein may include one or more immediate release components.

Uses and Therapeutic Methods

Suitably, the compositions of the invention contain floating IPN forming systems comprising at least one GHB drug, which systems form in vivo in the presence of an acid (e.g., stomach or gastric acid). Without wishing to be bound by theory, it is believed that the upon reaction with the acid, a gas generating agent in the composition forms a non-toxic gas which enables the IPN containing the biologically active moiety to remain in the stomach for at least 2 hours, preferably, about 3 hours to about 24 hours, or about 4 hours to about 16 hours, or about 6 hours to about 12 hours, or about 8 hours to about 10 hours, or about 2.5 hours to about 8 hours, or about 3 hours to about 6 hours, or about 4 to about 5 hours. During its retention in the stomach, the IPN provides modified release of the active moiety (e.g., GHB drug(s) and, optionally, other drug(s)) entrapped therein. Without wishing to be bound by theory, it is believed this retention time is caused by the floating IPN exceeding the size of the pyloric valve for at least two hours. Thus, it is believed that the composition forms a floating IPN of at least about 12 mm to 25 mm in width, at least about 15 mm in width, or about 20 mm in width for this length of time.

In certain embodiments, therapeutic methods are provided to treat conditions amenable to treatment by GHB, such as those discussed hereinabove, by administering an effective amount of one or more dosage forms of the invention.

The present dosage forms can be administered to treat a human afflicted with narcolepsy to reduce cataplexy and/or daytime sleepiness.

The present dosage forms can be administered to humans, particularly in the elderly (>50 years old), to improve the quality of sleep, or in conditions in which an increase in growth hormone levels in vivo is desired.

The compositions can also be used to treat fibromyalgia or chronic fatigue syndrome, e.g., to alleviate at least one symptom of fibromyalgia or chronic fatigue syndrome. See, U.S. Pat. No. 5,990,162.

The dosage forms described herein may be provided as a kit comprising, separately packaged, a container comprising an effective amount of the GHB composition in a sachet or other suitable package. For example, the powder may be packaged aluminum foil envelopes, or in a blister pack. The powder can be packaged in many conformations with or without desiccant or other materials to prevent ingress of water. Instruction materials or means, such as printed labeling, can also be included for their administration, e.g., sequentially over a preselected time period and/or at preselected intervals, to yield the desired levels of GHB in vivo for preselected periods of time, to treat a preselected condition.

A kit for treating a patient with a GHB drug, said kit comprising (a) a container comprising a powder composition as described herein; (b) a syringe; (c) a measuring cup; (d) a press-in-bottle adapter; optionally at least one empty pharmacy container with a child-resistant cap. In certain embodiments, the kit contains a suspending agent and/or purified water. In other embodiments, the kit includes a container for reconstituting the powder.

A daily dose of about the equivalent of about 1 mg/kg to about 50 mg/kg of sodium GHB can be administered to accomplish the therapeutic results disclosed herein. For example, a daily dosage of about 0.5 grams to about 20 grams of the GHB or the equivalent thereto can be administered, preferably about 1 grams to about 15 grams, in single or divided doses. In other embodiments, doses may range from about 1.5 grams to about 9 grams per night, about 4.5 g to about 7.5 g, or about 4 grams to 6 grams.

As noted herein above, the compositions may be useful in the treatment of a variety of conditions amenable to treatment by a GHB, such as narcolepsy to reduce cataplexy and/or daytime sleepiness, to improve the quality of sleep, or in conditions in which an increase in growth hormone levels in vivo is desired, and to treat fibromyalgia or chronic fatigue syndrome. The present dosage forms may be used to treat a host of other indications including drug and alcohol abuse, anxiety, cerebrovascular diseases, central nervous system disorders, neurological disorders including Parkinson's Disease and Alzheimer Disease, Multiple Sclerosis, autism, depression, inflammatory disorders, including those of the bowel, such as irritable bowel disorder, regional ileitis and ulcerative colitis, autoimmune inflammatory disorders, certain endocrine disturbances and diabetes.

The compositions may also be administered for the purpose of tissue protection including protection following hypoxia/anoxia such as in stroke, organ transplantation, organ preservation, myocardial infarction or ischemia, reperfusion injury, protection following chemotherapy, radiation, progeria, or an increased level of intracranial pressure, e.g. due to head trauma. The present dosage forms can also be used to treat other pathologies believed to be caused or exacerbated by lipid peroxidation and/or free radicals, such as pathologies associated with oxidative stress, including normal aging. See Patent Publication US 2004/0092455 A1. The c compositions may also be used to treat movement disorders including restless leg syndrome, myoclonus, dystonia and/or essential tremor. See Frucht et al, *Movement Disorders*, 20(10), 1330 (2005).

As described herein, the GHB compositions of the invention may be dosed orally once per day at bedtime, e.g., between 10 pm-12 pm. This is particularly well suited for treatment of narcolepsy. Optionally, smaller doses may be delivered at bedtime and at different intervals during the night, or in the morning and at intervals during the day. Other variations may be selected depending upon the patient and the indication being treated (e.g., fibromyalgia, etc).

As described herein, the powder compositions may be reconstituted and taken by the patient by drinking, eating with a spoon (e.g., pudding), or by spreading on toast or a cracker (e.g., paste), or by any suitable means.

In one embodiment particularly well suited for treatment of narcolepsy, total GHB in the composition is equivalent to about 4.5 to about 15 grams sodium GHB. In certain embodiments, the composition provides a therapeutic effect for about 3.5 to about 8 hours.

A "dissolution rate" refers to the quantity of drug released in vitro from a dosage form per unit time into a release medium. In vitro dissolution rates in the studies described herein were performed on dosage forms placed in a USP Type II or USP type 7 dissolution apparatus set to 37° C.±2° C. under suitable experimental conditions; see, e.g., US2012/007685, incorporated by reference herein. The dissolution media may be purified water, 0.1 N HCl, simulated gastric or intestinal fluid, or other media known in the art.

By "bioavailability" as used herein is intended to estimate area under the curve, or AUC of the active drug in systemic circulation after oral administration as a liquid suspension according to the invention. The AUC is affected by the extent to which the drug is absorbed in the GI tract.

Products are considered to be "bioequivalent" if the relative geometric mean ratio of $C_{max}$, $AUC_{(0-t)}$ and $AUC_{(0-\infty)}$ of the test product to reference product is within the 90% confidence interval of 80% to 125%.

By "sodium oxybate oral solution" is intended the product currently known as Xyrem®, a solution that contains 500 mg sodium oxybate/mL water, adjusted to a pH of 7.5 with malic acid.

The term "$AUC_{0-\infty}$" or "$AUC_{0-inf}$" means the area under the plasma concentration time curve from time 0 to infinity The term "$AUC_{0-\infty}$" or "$AUC_{inf}$" is the mean area under the plasma concentration-time curve extrapolated to infinity. It is calculated as the mean of the area under the plasma concentration-time curve from time zero extrapolated to infinity, calculated for each individual participating in the bioavailability study and may be the geometric or arithmetic mean. In general, the drug concentration is measured at certain discrete points in time and the linear trapezoidal rule is used to estimate AUC. Partial AUC may be useful in determining bioequivalence, where the AUC is determined based on a specific fragment of the $AUC_{0-\infty}$. These fragments may be, e.g., from 0-4 hours, 5-8 hours, under fasting and/or fed conditions, or at different intervals, including ½ hour, 1 hour, 4 hours, 6 hours, 7 hours or 8 hours.

"Bioequivalent" means the pharmacokinetic profile of a test composition is within the range of about 80% to about 125% for the 90% confidence interval, when compared to the geometric mean ratio values of one or more of the AUC or the $C_{max}$ of the reference composition.

As used herein, the term "equivalent" to sodium oxybate is used to refer to the molecular weight of a GHB portion of the GHB salt and/or anion exchange resin complex, without taking into account the molecular weight of the anion exchange resin or any matrix or coating component.

"$C_{max}$" the maximum blood concentration of the GHB active pharmaceutical ingredient after the drug has been orally administered. Unless otherwise specified, the Cmax values provided herein are geometric mean values.

As used herein, the ratio of $C_{max}$ to plasma concentration is determined by dividing the Cmax by the plasmid concentration: $C_{max}$ (mcg/mL)/plasma concentration (mcg/mL). In certain embodiments, an orally administrable composition is provided herein which comprising at least one GHB drug. Following administration of the composition to a human in need thereof, the floating IPN provides a ratio of $C_{max}$ to plasma concentration for the GHB drug(s) at 5 hours post dosing of less than 7, more preferably less than 6.

In certain embodiments, a composition provided herein is a floating IPN comprising GHB(s), which provide an pharmacokinetics of one or more of the following, as determined using geometric mean, AUCinf of about 181 mcg·hr/mL to about 282.5 mcg hr/mL, a Cmax of about 66.7 mcg/mL to about 104.2 mcg/mL, and/or a plasma concentration of about 13.7 mcg/mL to about 21.4 mcg/mL. In certain embodiments, a composition provided herein is a floating IPN comprising GHB(s), which provide an pharmacokinetics of one or more of the following, as determined using geometric mean, AUCinf of about 203 mcg·hr/mL to about 249 mcg hr/mL, a Cmax of about 75.1 mcg/mL to about 91.7 mcg/mL, and/or a plasma concentration of about 15.4 mcg/mL to about 18.8 mcg/mL. In certain embodiments, the pharmacokinetics include one or more of, as determined using geometric mean, AUCinf is about 226 mcg·hr/mL; the AUCt is about 224 g·hr/mL. Cmax of about 83.4 mcg/mL and a plasma concentration of about 17.1 mcg/mL.

In certain embodiments, a composition provided herein is a floating IPN comprising GHB(s), which provide an pharmacokinetics of one or more of the following, as determined using geometric mean, AUCinf of about 185 mcg·hr/mL to about 289 mcg hr/mL, a Cmax of about 73.8 mcg/mL to about 115 mcg/mL, and/or a plasma concentration of about 17.1 mcg/mL to about 26.8 mcg/mL. In certain embodiments, a composition provided herein is a floating IPN comprising GHB(s), which provide an pharmacokinetics of one or more of the following, as determined using geometric mean, AUCinf of about 208 mcg·hr/mL to about 254 mcg hr/mL, a Cmax of about 83.0 mcg/mL to about 101 mcg/mL, and/or a plasma concentration of about 19.3 mcg/mL to about 23.5 mcg/mL. In certain embodiments, the pharmacokinetics include one or more of, as determined using geometric mean, AUCinf is about 231 mcg·hr/mL; the AUCt is about 228 g·hr/mL. Cmax of about 92.2 mcg/mL and/or a plasma concentration of about 21.4 mcg/mL.

The term "mean maximum plasma concentration" (mean $C_{max}$) is defined for the purposes of the present invention as the maximum mean blood drug concentration.

"Mean plasma concentration" is the arithmetic mean blood plasma concentration.

Such profiles are especially desirable for diseases such as narcolepsy, cataplexy, movement disorders such as essential tremor and restless leg syndrome, fibromyalgia and chronic fatigue syndrome.

The term "area under the curve (AUC)t" or (0-t) refers to the total drug exposure over time starting at the time the drug is administered and up to 24 hours. In general, the drug concentration is measured at certain discrete points in time and the linear trapezoidal rule is used to estimate AUC.

The term "Tmax" refers to a term used in pharmacokinetics refers to the maximum (or peak) blood concentration that a drug achieves at the time the Cmax is observed.

The words "comprise", "comprises", and "comprising", and "contain", "containing", and "contains" are to be interpreted inclusively rather than exclusively. The words "consist", "consisting", and its variants, are to be interpreted exclusively, rather than inclusively.

As used herein in reference to numeric values provided herein, the term "about" may indicate a variability of as much as 10%.

While the invention has been described with reference to exemplary embodiments, it will be understood by those skilled in the art that various changes may be made and equivalents may be substituted for elements thereof without departing from the scope of the invention. Details of the present invention, including its objects and advantages, are provided in the non-limiting exemplary illustrations below.

EXAMPLES

The following examples are illustrative only and are not intended to be a limitation on the present invention.

Example 1

Oxybate ER POS Containing API as API-Resin Complex

I. Preparation of Drug Resin Complex

| Ingredients | Gm |
|---|---|
| Sodium oxybate | 18.35 |
| Cholestyramine | 81.65 |

Weighed quantity of Sodium oxybate is dissolved in 100 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of Coated Drug-Resin Complex

| Ingredients | Gm |
|---|---|
| GHB resinate | 50.00 |
| Kollicoat® SR30D polyvinylacetate dispersion blend | 23.82 |
| Triacetin | 1.18 |

Triacectin is added in purified water under stirring and continue stirring to get clear solution. Triacetin solution is added gradually to Kollicoat® SR30D dispersion under stirring and continue stirring for 1 hr. The coating dispersion is screened through sieve #40 and stirring is continued throughout the coating process. GHB resinate coated using Kollicoat® coating dispersion in Fluid Bed Coater and coated complex is dried at 60° C. Coated complex is passed through #40 screen.

Preparation of ER POS
Composition of GHB Resinate ER POS

| No. | Ingredients | Gm/per dose equivalent to 2.25 gm sodium oxybate |
|---|---|---|
| 1. | GHB resinate uncoated | 6.13 |
| 2. | GHB resinate coated | 9.2 |
| 3. | Carrageenan kappa | 1.2 |
| 4. | Carrageenan iota | 1 |
| 5. | Pectin | 1 |
| 6. | Guar gum | 1 |
| 7. | Borax | 0.3 |
| 8. | Calcium carbonate | 1 |
| 9. | Potassium citrate | 0.3 |
| 10. | Co-Povidone | 0.6 |
| 11. | HPMC low viscosity | 0.05 |
| 12. | Sucralose | 0.05 |
| 13. | Mannitol | 0.3 |
| 14. | Talc | 0.1 |
| 15. | Sodium benzoate | 0.01 |
| 16. | Banana flavor | 0.04 |
| 17. | Purified water, USP | 80 gm |

III. Weighed quantities of drug-resin complex of step I, coated drug-resin complex of step II, excipients 3 to 9 are mixed and then granulated using aqueous solution of co-povidone. Granules are dried in fluid bed processor at 45° C. and screened through #30 sieve.

IV. The granules of step III are mixed with weighed and screened (#40) quantities of HPMC K100LV, banana flavor, talc, sodium benzoate, mannitol and sucralose. This blend to be reconstituted using 80 gm purified water for dose equivalent to 2.25 gm sodium oxybate.

In-Vitro Testing:

I. Onset and Duration of Duration of Floating

Amount of suspension equivalent to 4.5 gm sodium oxybate is added to 500 ml SGF without enzyme. The anticipated time required for raft to float and duration of floating are as follows.

| Onset of floating (minutes) | ≤20 |
| Duration of floating (hours) | 12 |

II. Resiliency of the Raft

Amount of suspension equivalent to 4.5 gm sodium oxybate is added to 500 ml SGF without enzyme 0.1N HCl solution. Then it is subjected to agitation using mechanical shaker set at 37° C. and 75 rpm. Anticipated Observation: The raft retains integrity for a period of 12 hours.

III. In Vitro Release Study

Figure 2:
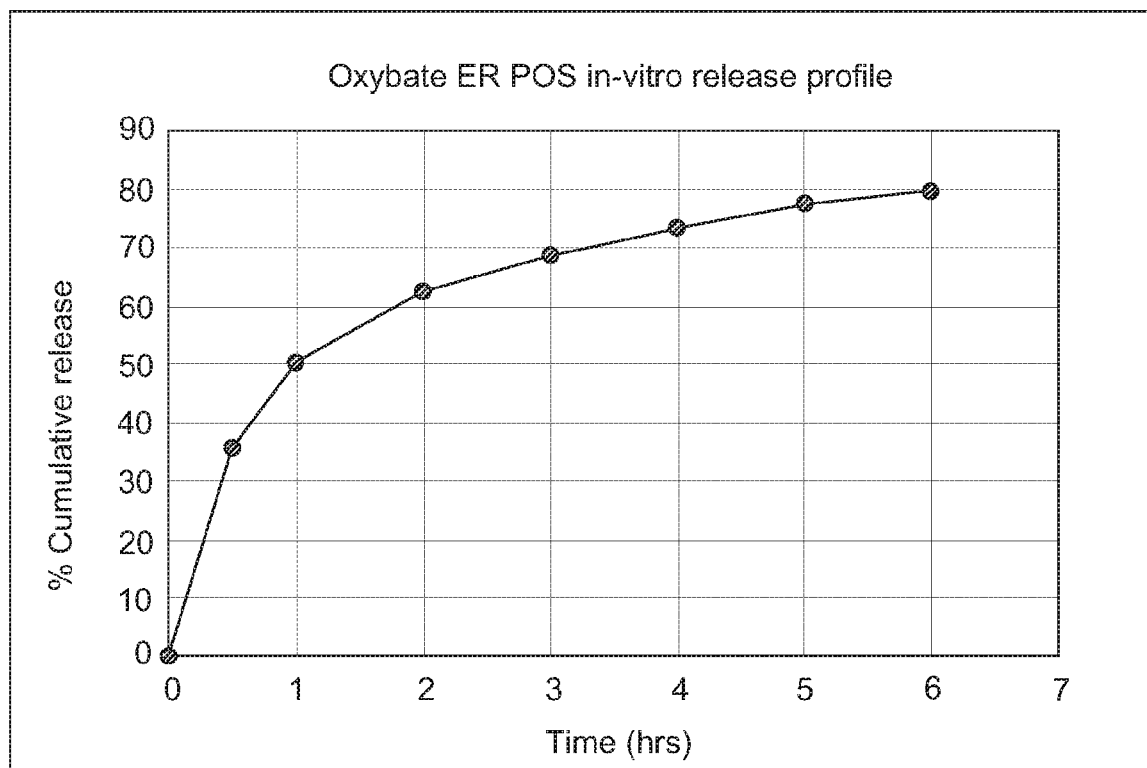
FIG. 2 illustrates the anticipated in vitro dissolution profile for sodium oxybate in the powder-for-suspension formulation of Example 1 over a period of 6 hours (time in hours provided on x axis), with percentage (%) cumulative release provided on the y axis.

Dissolution studies are performed using USP Apparatus Type II set at 50 rpm and 37° C. and 500 ml SGF without enzyme as medium with ion replenishment to maintain ionic sink. Amount of reconstituted suspension equivalent to 4.5 gm sodium oxybate is added to dissolution medium. Sampling points: 1, 2, 3, 4, 6 hours. The anticipated curve is provided in FIG. 2.

Example 2

Oxybate ER POS Containing API Partly in the Form of Complex with Anion Exchange Resin and Partly in the Form of Sodium Salt I. Preparation of drug resin complex

| Ingredients | Gm |
| --- | --- |
| Sodium oxybate | 18.35 |
| Cholestyramine | 81.65 |

Weighed quantity of Sodium oxybate is dissolved in 100 ml water. Weight quantity of the resin is added to drug solution under stirring and stirring is continued further for a period of 4 hr. Drug-resin complex is isolated by filtration and dried at 60° C. Drug-resin complex is passed through #60 screen.

II. Preparation of Coated Drug-Resin Complex

| Ingredients | Gm |
| --- | --- |
| GHB resinate | 50.00 |
| Kollicoat® SR30D | 23.82 |
| Triacetin | 1.18 |

Triacectin is added in purified water under stirring and continue stirring to get clear solution. Triacetin solution is added gradually to Kollicoat® SR30D dispersion under stirring and continue stirring for 1 hr. The coating dispersion is screened through sieve #40 and stirring is continued throughout the coating process. GHB resinate is coated using Kollicoat® coating dispersion in Fluid Bed Coater and coated complex is dried at 60° C. Coated complex is passed through #40 screen.

Preparation of ER POS

Composition of GHB Resinate ER POS

| No. | Ingredients | Gm/per dose equivalent to 2.25 gm sodium oxybate |
| --- | --- | --- |
| 1. | Sodium oxybate | 1.125 |
| 2. | GHB resinate coated | 9.2 |
| 3. | Carrageenan kappa | 0.9 |
| 4. | Carrageenan iota | 0.75 |
| 5. | Pectin | 0.5 |
| 6. | Guar gum | 0.75 |
| 7. | Borax | 0.3 |
| 8. | Calcium carbonate | 0.75 |
| 9. | Potassium citrate | 0.25 |
| 10. | Co-Povidone | 0.45 |
| 11. | HPMC low viscosity | 0.05 |
| 12. | Sucralose | 0.05 |
| 13. | Mannitol | 0.3 |
| 14. | Talc | 0.1 |
| 15. | Sodium benzoate | 0.01 |
| 16. | Banana flavor | 0.04 |
| 17. | Purified water, USP | 60 gm |

III. Weighed quantities of drug-resin complex of step I, coated drug-resin complex of step II, excipients 3 to 9 are mixed and then granulated using aqueous solution of co-povidone. Granules are dried in fluid bed processor at 45° C. and screened through #30 sieve.

IV. The granules of step III are mixed with weighed and screened (#40) quantities of HPMC K100LV, banana flavor, talc, sodium benzoate, mannitol and sucralose. The blend is to be reconstituted using 60 gm purified water at the time of administration.

In-Vitro Testing:

I. Onset and Duration of Duration of Floating

Amount of suspension equivalent to 2.25 gm sodium oxybate is added to 500 ml SGF without enzyme. The anticipated time required for raft to float and duration of floating follow.

II. Resiliency of the Raft

Amount of suspension equivalent to 2.25 gm sodium oxybate is added to 500 ml SGF without enzyme. Then it is subjected to agitation using mechanical shaker set at 37° C. and 75 rpm. Anticipated Observation: The raft retains integrity for 12 hours.

| Onset of floating (minutes) | ≤18 |
| Duration of floating (hours) | 12 |

In a test using the components identified above except the flavorants (items 12-16), formation of the raft was observed within about 2 minutes and floating was observed throughout the tested time period of 12 hours.

III. In Vitro Release Study

Figure 3:
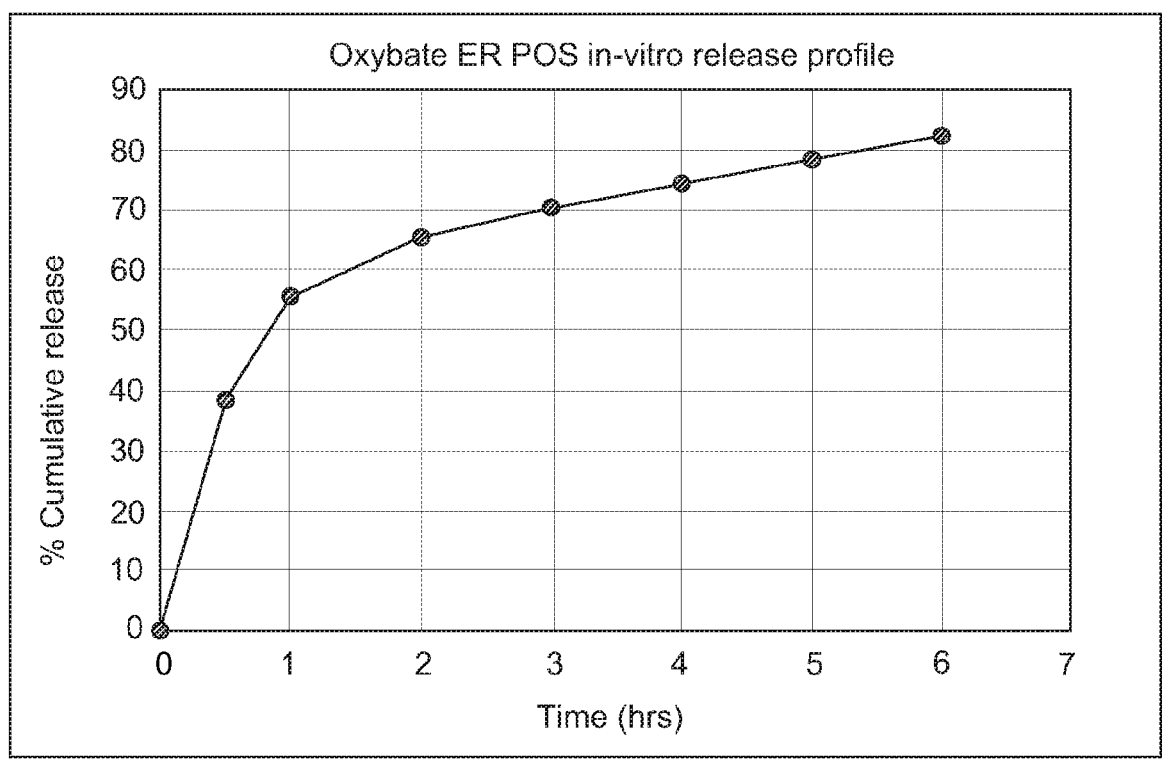
FIG. 3 illustrates the anticipated in vitro dissolution profile for sodium oxybate in the powder-for-suspension formulation of Example 2 over a period of 6 hours (time in hours provided on x axis), with percentage (%) cumulative release provided on the y axis.

Dissolution studies are performed using USP Apparatus Type II set at 50 rpm and 37° C. and 500 ml SGF without enzyme as medium with ion replenishment to maintain ionic sink. Amount of reconstituted suspension (60 gm) equivalent to 2.25 gm sodium oxybate is added to dissolution medium. Sampling points: 1, 2, 3, 4, 6 hours. The anticipated curve is provided in FIG. 3.

Example 3

Oxybate ER POS Containing API in the Form of Sodium Salt

I. Preparation of ER Granules

| Ingredients | Gm |
| --- | --- |
| Sodium oxybate | 100 |
| Kollidon® SR | 30 |
| Co-Povidone | 6 |

Weighed quantity of sodium oxybate, Kollidon® SR and 3.0 gm of co-povidone are mixed for 15 min. The remaining amount of Co-povidone is dissolved in 15 purified water. The blend is granulated using co-povidone solution. Wet granules are dried in hot air over at 60° C. Dried granules are passed through #30 screen and then through #60 screen.

II. Preparation of Coated ER Granules

| Ingredients | Gm |
| --- | --- |
| ER granules of step I | 100.00 |
| Kollicoat® ® SR30D | 47.64 |
| Triacetin | 2.36 |

Triacectin is added in purified water under stirring and continue stirring to get clear solution. Triacetin solution is added gradually to Kollicoat® SR30D dispersion under stirring and continue stirring for 1 hr. The coating dispersion is screened through sieve #40 and stirring is continued throughout the coating process. ER granules of step I are coated using Kollicoat® coating dispersion in Fluid Bed Coater and coated complex is dried at 60° C. Coated complex is passed through #40 screen.

Preparation of ER POS
Composition of Sodium Oxybate ER POS

| No. | Ingredients | Gm/per dose equivalent to 2.25 gm sodium oxybate |
| --- | --- | --- |
| 1. | ER granules of step I | 1.36 |
| 2. | Coated ER granules of step II | 1.875 |
| 3. | Fenugreek gum | 0.6 |
| 4. | Carrageenan iota | 0.65 |
| 5. | Pectin | 0.65 |
| 6. | Guar gum | 0.6 |
| 7. | Borax | 0.6 |
| 8. | Calcium carbonate | 0.40 |
| 9. | Calcium chloride | 0.40 |
| 10. | Co-Povidone | 0.45 |
| 11. | HPMC K100LV | 0.05 |
| 12. | Sucralose | 0.05 |
| 13. | Mannitol | 0.75 |
| 14. | Talc | 0.1 |
| 15. | Sodium benzoate | 0.01 |
| 16. | Banana flavor | 0.04 |
| 17. | Purified water, USP | 40 gm |

III. Weighed quantities of ER granules of step I, coated ER granules of step II, fenugreek gum, pectin, carrageenan iota, guar gum, calcium carbonate, calcium chloride are granulated using 10 gm aqueous solution containing borax and co-povidone. Granules are dried at 60° C. in hot air oven. Dried granules are passed through #40 screen.

IV. The granules of step III are mixed with weighed and screened (#40) quantities of HPMC K100LV, banana flavor, talc, sodium benzoate, mannitol and sucralose. This blend is reconstituted using 40 gm purified water.

In-Vitro Testing:

I. Onset and Duration of Duration of Floating

Amount of reconstituted suspension equivalent to 2.25 gm sodium oxybate is added to 500 ml SGF without enzyme. The anticipated time required for raft to float and duration of floating are as follows.

| Onset of floating (minutes) | ≤20 |
| --- | --- |
| Duration of floating (hours) | 12 |

II. Resiliency of the Raft

Amount of reconstituted suspension equivalent to 2.25 gm sodium oxybate is added to 500 ml SGF without enzyme. Then it is subjected to agitation using mechanical shaker set at 37° C. and 75 rpm. Anticipated Observation: The raft retains integrity for a period of 12 hours.

Example 4

Oxybate ER POS with Equivalent to 4.5 g Sodium Oxybate—Floating IPN Having Anionic Polymers A. Preparation of ER Granules with Oxybate—Anion Ion Exchange Resin Complex (Resinate)

| Ingredients | G/batch |
| --- | --- |
| Sodium Oxybate | 400.0 |
| Purified Water, USP | 1.8 L |
| Cholestyramine Resin, USP (Duolite™ AP143/1016) | 400.0 |
| Purified Water, USP | NA |

Sodium oxybate was dissolved in purified water (about 18% w/w) with continuous stirring. The cholestyramine resin was added to it gradually. Stirring was continued at room temperature for 4 hours. The dispersion was filtered to remove excess of sodium oxybate and the counter ions. The resulting wet resinate then dispersed in about 18% purified water (1.8 L purified water) containing 400.0 grams of sodium oxybate and stirred for four hours. Following this second round of complexing, the wet resinate was filtered and washed two times, each time with 1.8 L purified water, followed by further filtering to remove the water used for washings. This process was repeated two further times, for a total of four stages of complexing, filtering and washing. At the completion of these rounds, the wet resinate was dried for a target loss on drying percentage (% LOD) of 7% w/w followed by screened through a #40 sieve.

The % assay of resinate was found to be 27.3% w/w of Oxybate (eq. to 33.4% w/w of Sodium Oxybate) and % LOD was about 3.8% w/w.

B. Preservative Granules

| Ingredients | G/Unit | % w/w |
| --- | --- | --- |
| Copovidone, NF (Kollidon ® VA 64) | 0.20 | 5.26 |
| Sucralose, NF | 0.36 | 9.47 |
| Propylparaben Sodium, NF | 0.04 | 1.05 |
| Methylparaben Sodium, NF | 0.20 | 5.26 |
| Microcrystalline Cellulose, NF (Avicel ® PH 102) | 2.25 | 59.21 |
| Mannitol USP (Pearlitol™ 100SD) | 0.75 | 19.74 |
| Purified Water, USP[1] (removed during processing) | Q.S. | — |
| Total | 3.80 | 100.00 |

Purified water was weighed and kept on stirring using overhead stirrer. Copovidone was added to it on stirring and stirring continued to get clear solution. Sucralose was added to it and stirring continued to get clear solution. Propylparaben Sodium and Methylparaben Sodium were dissolved in Purified water and the solution was added to step-1 solution (used as a binder solution). Microcrystalline Cellulose and Mannitol were screened through Sieve #40 and mixed in High shear granulator. The blend was granulated using the step-2 binder solution. Purified water was added as needed. The wet granular mass was then dried in Fluid Bed Dryer to achieve the % LOD less than 2% w/w. the dried granules were sized through Sieve #40. The % LOD was found to be 1.87% w/w and Preservative contents were found to be 104.1% and 97.3% for Methylparaben Sodium and Propylparaben Sodium respectively.

C. Slower Release Formulation:

This formulation is designed to have a gradual onset of oxybate release. Matrix Granules were prepared using a roll compaction process, as follows.

| Ingredients | Batch Size 440.0 g | |
| --- | --- | --- |
| | G/Unit | % w/w |
| Hypromellose, USP (METHOCEL ™ K100M premium Hydroxypropyl Methylcellulose) | 1.50 | 13.64 |
| Crospovidone NF, (Kollidon ® CL), Type A | 1.40 | 12.73 |
| Pectin (GENU ™ Pectin LM-HC-25 AS) | 1.70 | 15.45 |
| Gellan Gum (Kelcogel ® F) | 1.10 | 10.00 |
| Carbomer Homopolymer Type A (Carbopol ™ 71G Polymer) NF | 1.10 | 10.00 |
| Potassium Bicarbonate USP Anhydrous | 0.80 | 7.27 |
| Calcium Chloride Dihydrate USP | 0.80 | 7.27 |
| Copovidone, NF (Kollidon ® VA 64) | 0.45 | 4.09 |
| Microcrystalline Cellulose, NF (Avicel ® PH 102) | 2.15 | 19.55 |
| Total | 11.00 | 100.00 |

All the ingredients were weighed and co-sifted through Sieve #40. The co-sifted ingredients were mixed in 4 L Cube blender at 35 RPM for 10 minutes. The resulting blend was roll compacted using Roll Compactor at about 1200 PSI Roll pressure. The roll compacts were then screened through Sieve #40. The screened granules were again roll compacted at 1200 PSI Roll pressure. The roll compacts were screened through Sieve #40.

D. Final Slower Release Composition

This formulation is designed to have a slower onset of oxybate release. Matrix Granules were prepared using a roll compaction process, as follows.

| Ingredients | Batch Size 900.0 g (30 Units) | |
| --- | --- | --- |
| | G/Unit | % w/w |
| Oxybate-cholestyramine resinate, prepared as in Part A (containing 27% w/w oxybate, equiv to 4.5 g sodium oxybate) | 13.68 | 45.60 |
| Preservative granules | 3.80 | 12.67 |
| Matrix Former-Granules | 11.00 | 36.67 |
| Microcrystalline Cellulose, NF (Avicel ® PH 102) | 1.42 | 4.73 |
| Talc, USP | 0.10 | 0.33 |
| Total | 30.00 | 100.00 |

All the ingredients from the preceding table were weighed and co-sifted through Sieve #40. The blend of step-1 was mixed in 4 L Cube blender at 30 RPM for 10 minutes. This affords the final product.

Figure 4:
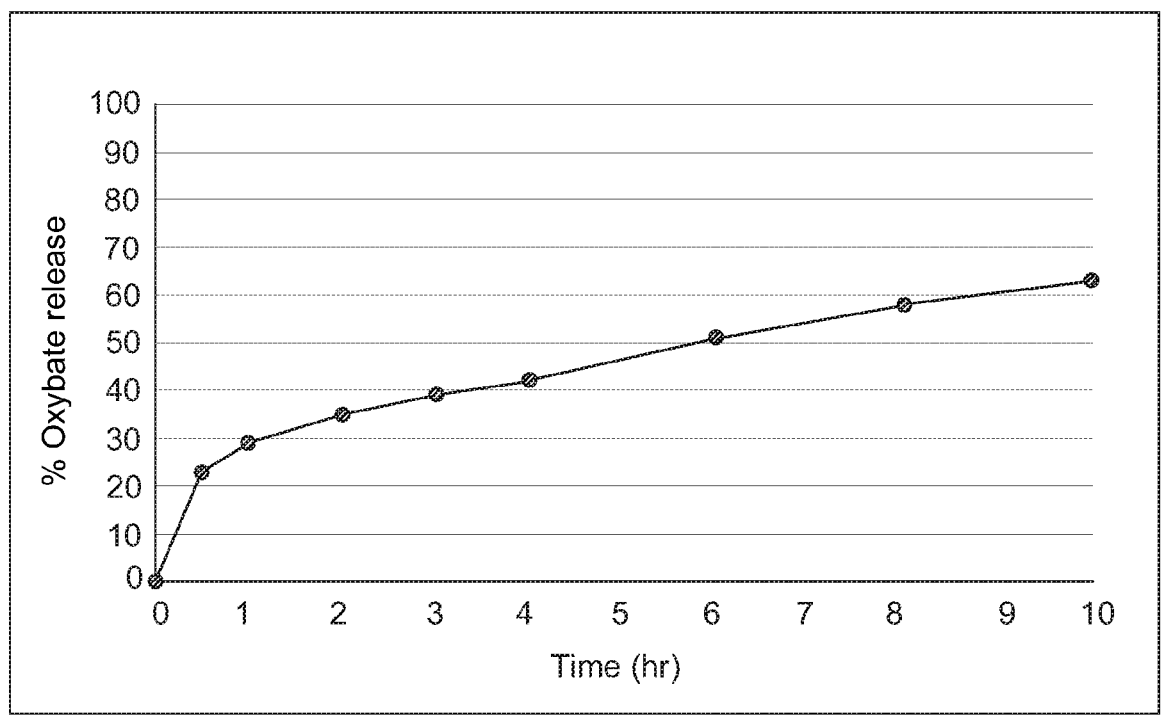
FIG. 4 provides the in vitro dissolution profile for sodium oxybate in the powder-for-suspension slower release formulation of Example 4 in a 3-tier dissolution medium under the following conditions: USP App. II (Paddle), 75 RPM, 650 mL (0.03 N HCl+430 mg KCl)+20 mL water after sample addition, Addition of 50 mL of 5.3% w/w Potassium Chloride solution after 2-hr sampling and addition of 100 mL of 4.55% w/w KCl solution after 4-hr sampling. Release over a period of 10 hours is shown.

The dissolution study was conducted in 3-tier dissolution medium. USP App. II (Paddle), 75 RPM, 650 mL (0.03 N HCl+430 mg KCl)+20 mL water after sample addition, Addition of 50 mL of 5.3% w/w Potassium Chloride solution after 2-hr sampling and addition of 100 mL of 4.55% w/w KCl solution after 4-hr sampling. The release profile is depicted in FIG. 4.

E. Faster Release Composition

This formulation is designed to have a faster onset of oxybate release. Matrix Granules were prepared using a roll compaction process, as follows.

1. Matrix Granules for Faster Release Composition

| Ingredients | Batch Size 330.0 g | |
| --- | --- | --- |
| | G/Unit | % w/w |
| Hypromellose, USP (METHOCEL ™ K100M premium Hydroxypropyl Methylcellulose) | 0.70 | 12.73 |
| Carrageenan, NF (Gelcarin ® GP-911, NF) | 0.65 | 11.82 |
| Pectin (GENU ™ Pectin LM-HC-25 AS) | 0.70 | 12.73 |
| Gellan Gum (Kelcogel ™ F) | 0.65 | 11.82 |
| Carbomer Homopolymer Type A (Carbopol ™ 71G Polymer) NF | 0.70 | 12.73 |
| Potassium Bicarbonate USP Anhydrous | 0.65 | 11.82 |
| Calcium Chloride Dihydrate USP | 0.55 | 10.00 |
| Copovidone, NF (Kollidon ® VA 64) | 0.25 | 4.55 |
| Microcrystalline Cellulose, NF (Avicel ® PH 102) | 0.65 | 11.82 |
| Total | 5.50 | 100.00 |

All the ingredients were weighed and co-sifted through Sieve #40. The co-sifted ingredients were mixed in a 4 L Cube blender at 35 RPM for 10 minutes. The blend was roll compacted using Roll Compactor at about 1200 PSI Roll pressure. The roll compacts were then screened through Sieve #40. The screened granules were again roll compacted at 1200 PSI Roll pressure. The roll compacts were screened through Sieve #40.

2. Fast-Release Composition

| Ingredients | Batch Size 735.0 g (30 Units) | |
| --- | --- | --- |
| | G/Unit | % w/w |
| Oxybate-cholestyramine resinate, prepared as in part A (containing 26% w/w oxybate, equiv to 4.5 g sodium oxybate) | 13.68 | 55.84 |
| Preservative granules | 3.80 | 15.51 |
| Matrix Former-Granules for Prototype II | 5.50 | 22.45 |
| Microcrystalline Cellulose, NF (Avicel ® PH 102) | 1.42 | 5.80 |
| Talc, USP | 0.10 | 0.41 |
| Total | 24.50 | 100.0 |

All the ingredients were weighed and co-sifted through Sieve #40. The co-sifted blend was mixed in 4 L Cube blender at 30 RPM for 10 minutes.

Figure 5:
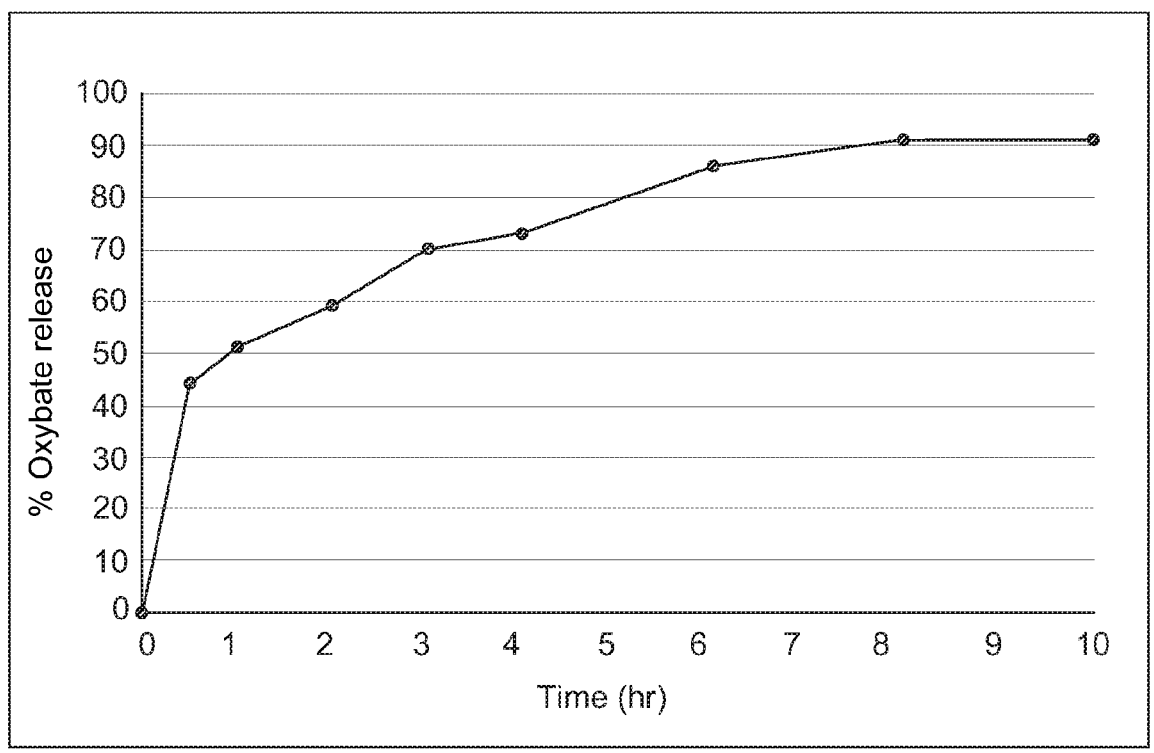
FIG. 5 provides the in vitro dissolution profile for sodium oxybate in the powder-for-suspension the faster release formulation of Example 4 in a 3-tier dissolution medium under the following conditions: USP App. II (Paddle), 75 RPM, 650 mL (0.03 N HCl+430 mg KCl)+20 mL water after sample addition, Addition of 50 mL of 5.3% w/w Potassium Chloride solution after 2-hr sampling and addition of 100 mL of 4.55% w/w KCl solution after 4-hr sampling. Release over a period of 10 hours is shown.

Dissolution study was conducted in 3-tier dissolution medium. The release profile is in FIG. 5.

F. Pharmacokinetic Studies in Healthy Human Volunteers

Design: An open label, randomized, two-way cross-over, single dose pilot study to evaluate relative bioavailability of two oxybate extended release formulations (n=11) administered after 8 hr fasting. Treatment A: slow release formulation, Treatment B: fast release formulation

| Parameters (geometric mean) | Treatment A (Slow-Release Composition) | Treatment B (Fast-Release Composition) |
| --- | --- | --- |
| $AUC_{inf}$ (mcg · hr/mL) | 226.49 | 230.57 |
| $AUC_t$ (mcg · hr/mL) | 224.03 | 228.08 |
| Cmax (mcg/ml) | 83.42 | 92.25 |
| Plasma concentration at 5 hour post dosing (mcg/ml) | 17.12 | 21.45 |

Example 5

Oxybate ER POS, eq. to 9 g of Sodium Oxybate

A. Preservative Granules

| Ingredients | % w/w |
| --- | --- |
| Propylparaben Sodium, NF | 2.00 |
| Methylparaben Sodium, NF | 10.00 |
| Copovidone, NF (Kollidon ® VA64) | 10.00 |
| Sucralose | 18.00 |
| Mannitol, USP (Pearlitol ® SD100) | 25.00 |
| Microcrystalline Cellulose, NF (Avicel ® PH 102) | 35.00 |
| Purified water | Q.S. |
| Total | 100.00 |

Purified water was weighed and half of the Copovidone quantity was added to it on stirring. Stirring was continued to get clear solution. Propylparaben Sodium was added to it gradually on stirring and stirring continued to get clear solution. Methylparaben sodium was then added gradually. Stirring was continued to get clear solution. Microcrystalline cellulose, Mannitol, Sucralose and half of the required quantity of Copovidone were weighed and sifted through Sieve #40. The blend was mixed in high shear granulator for 5 minutes followed by granulated using step-1 solution. Purified water was added as needed.

The wet granular mass was dried in fluid bed system below % LOD of 2% w/w. the dried granules were screened through Sieve #40.

B. Matrix-Former Granules

| Ingredients | % w/w |
| --- | --- |
| Hypromellose, USP (Methocel ® K100M premium) | 16.67 |
| Crospovidone, NF (Kollidon ® CL) | 2.22 |
| Pectin (GENU ™ Pectin LM-HC-24 AS) | 18.89 |
| Gellan gum (Kelcogel ® F) | 12.22 |
| Carbomer Homopolymer Type A (Carbopol ® 71G) | 12.22 |
| Potassium Bicarbonate USP Anhydrous | 8.89 |
| Calcium chloride Dihydrate, USP | 8.89 |
| Copovidone, NF (Kollidon ® VA 64) | 4.44 |
| Microcrystalline Cellulose, NF (Avicel ® PH 102) | 15.56 |
| Total | 100.00 |

Procedure: All the ingredients were weighed and co-sifted through Sieve #40. The blend was mixed in Cube blender for 10 minutes at 35 RPM. The blend was roll compacted at about 1200 PSI pressure to get ribbon-like slugs. The slugs were screened through Sieve #40. The granular mass was roll compacted again at about 1200 PSI pressure and the slugs were screened through Sieve #40.

C. Oxybate ER POS, eq. to 9 g of Sodium Oxybate

| Ingredients | % w/w |
| --- | --- |
| Oxybate-cholestyramine resinate, CI[1] | 70.10 |
| Matrix Former-Granules | 21.95 |
| Preservative Granules | 4.88 |
| Microcrystalline Cellulose, NF (Avicel ® PH 102) | 1.37 |
| Mannitol, USP (Pearlitol ® SD100) | 1.46 |
| Talc | 0.24 |
| Total | 100.00 |

[1]eq. to 9 g of Sod. Oxybate (i.e. 7.358 g of Oxybate), Assay: 25.6% w/w Oxybate Procedure: All the ingredients were weighed and co-sifted through Sieve #40. The blend was mixed and filled into glass bottle for the eq. weight. The dissolution of the reconstituted product was studied as below—Reconstitution: Oxybate ER POS eq. to 9 g of Sodium Oxybate was reconstituted using 140 mL of Purified water and used for dissolution study. Dissolution conditions: Dissolution apparatus with 2 L vessels, 100 RPM (paddle), 1600 mL 0.02 N HCl.

| Time (hr) | % oxybate Release |
| --- | --- |
| 0.5 | 34 |
| 1 | 44 |
| 2 | 55 |
| 3 | 60 |
| 4 | 65 |
| 6 | 69 |
| 8 | 75 |
| 10 | 80 |

All patents, patent publications, and other publications listed in this specification, are incorporated herein by reference. Also incorporated by reference are priority documents, U.S. Patent Application No. 62/728,764, filed Sep. 8, 2018 and U.S. Patent Application No. 62/607,151, filed Dec. 18, 2017. While the invention has been described with reference to a particularly preferred embodiment, it will be appreciated that modifications can be made without departing from the spirit of the invention. Such modifications are intended to fall within the scope of the appended claims.

The invention claimed is:

1. An orally administrable gamma hydroxybutyrate drug composition which comprises a floating inter-penetrating network (IPN) forming system comprises:
  (a) at least one gamma hydroxybutyrate (GHB) drug which is at least one of GHB or a salt, hydrate, tautomer, or solvate, or complex thereof;
  (b) an inter-penetrating network (IPN) forming blend which self-assembles into a floating IPN in situ following oral ingestion, which comprises:
    (i) at least two polymers comprising at least one IPN forming anionic polymer and/or at least one IPN forming galactomannan polysaccharide;
    (ii) at least one cross-linking agent which interacts with the at least one IPN forming anionic polymer or galactomannan (i) to form an IPN and/or a further crosslinked IPN; and
  (c) a non-toxic gas generating agent, wherein the gas generating agent forms a non-toxic gas when exposed to stomach acid,
  wherein following oral ingestion, the composition provides a floating IPN which comprises the gamma hydroxybutyrate drug and the non-toxic gas entrapped therein, thereby providing a floating IPN, and
  wherein the GHB drug composition provides a ratio of Cmax to plasma concentration for the GHB drug(s) at 5 hours post dosing of less than 7 in healthy human volunteers after 8 hours fasting.

2. The orally administrable drug composition according to claim 1, wherein the self-assembling IPN forming blend comprises:
(a) at least two anionic polymers and at least one cross linking agent;
(b) at least one anionic polymer, at least one galactomannan, and at least two cross linking agents;
(c) at least one galactomannan, at least one anionic polymer, at least one non-ionic polymer and at least two cross linking agents;
(d) at least one galactomannan, at least two anionic polymers, at least one non-ionic polymer and at least two cross linking agents;
(e) at least two galactomannan polymers and at least one cross linking agent;
(f) at least two galactomannan polymers, at least one anionic polymer and at least two cross linking agents;
(g) at least two galactomannan polymers, at least one anionic polymer, at least one non-ionic polymer and at least two cross linking agents;
(h) at least two galactomannan polymers, at least one non-ionic polymer and at one cross linking agent;
(i) at least one anionic polymer, at least one galactomannan, and at least two cross linking agents;
(j) at least one anionic polymer, at least one galactomannan, and at least two cross linking agents at least one of which is pH dependent cross-linking agent;
(k) at least one galactomannan, at least one anionic polymer, at least one non-ionic polymer and at least two cross linking agents;
(l) at least one galactomannan polysaccharide, at least two anionic polymers, at least one non-ionic polymer and at least two cross linking agents;
(m) at least two galactomannan polymers, at least one anionic polymer and at least two cross linking agents, at least one of which is a pH-dependent cross-linking agent; or
(n) at least two galactomannan polymers, at least one anionic polymer, at least one non-ionic polymer and at least two cross linking agents, at least one of which is a pH-dependent cross-linking agent.

3. The orally administrable drug composition according to claim 1, wherein the IPN forming blend comprises at least one anionic polymer and at least a second polymer which are at least partially crosslinked with a crosslinking agent selected from sodium alginate, carrageenan I, pectin, gellan gum, alginic acid, carrageenan k, sodium carboxymethylcellulose, xanthan gum, or combinations thereof.

4. The orally administrable drug composition according to claim 1, wherein the IPN forming blend comprises at least one galactomannan polysaccharide which is at least partially cross-linked with borax, glutaraldehyde, or zirconium, divalent and trivalent metal salts, or combinations thereof.

5. The orally administrable drug composition according to claim 4, wherein the galactomannan is selected from guar gum, fenugreek gum, locust bean gum, or combinations thereof.

6. The orally administrable drug composition according to claim 1, wherein the gas-generating agent is selected from carbonates or bicarbonates of an alkali or alkaline earth metal, sulfites, or combinations thereof, or combinations thereof with an acid source which create a gas-generating couple.

7. The orally administrable drug composition according to claim 6, wherein the carbonate or bicarbonate of an alkali or alkaline earth metal are selected from potassium carbonate, potassium bicarbonate, sodium carbonate, sodium bicarbonate, calcium carbonate, sodium glycine carbonate, magnesium carbonate, or aluminum carbonate.

8. The composition according to claim 1, wherein the floating IPN provides extended release for at least about 3 hours to about 24 hours.

9. The composition according to claim 1, wherein the drug is present in more than one form.

10. The composition according to claim 9, wherein the composition comprises an immediate release and a controlled release form of the drug.

11. The composition according to claim 1 which is a powder, pudding paste, suspension, tablet or capsule.

12. The composition according to claim 1, wherein the composition is a suspension.

13. The composition according to claim 1, wherein the composition is a modified release composition.

14. A reconstituted product comprising (a) an extended release powder for reconstitution comprising a composition according to claim 1 and (b) water wherein the ratio, by weight, of the composition to water is 1:0.1 to 1:15, or 1:0.5 to 1:10, or 1:2 to 1:7.

15. An orally administrable composition according to claim 1 comprising at least one GHB drug that provides a ratio of Cmax to plasma concentration for the GHB drug(s) at 5 hours post dosing of less than 6 in healthy human volunteers after 8 hours fasting.

16. A method of treating a patient with narcolepsy, and/or reducing cataplexy and/or daytime sleepiness with composition according to claim 1.

17. The method of treating a patient according to claim 16, wherein the composition comprises 1 gram to 9 grams of the gamma hydroxybutyrate drug, based on equivalence to sodium oxybate.

18. A method of treating a patient with fibromyalgia, chronic fatigue syndrome, sleep apnea, Parkinson's disease, schizophrenia, binge eating, essential tremor and non-Parkinson's movement disorders, chronic cluster headache, and/or reducing constipation associated with opioids and opioid-related drugs with composition according to claim 1.

19. An orally administrable composition according to claim 1 comprising at least one GHB drug that provides a ratio of Cmax to plasma concentration for the GHB drug(s) at 5 hours post dosing of 1.5 to 5.5 in healthy human volunteers after 8 hours fasting.

* * * * *